(12) United States Patent
Ruoslahti et al.

(10) Patent No.: US 9,061,079 B2
(45) Date of Patent: Jun. 23, 2015

(54) PEPTIDES THAT HOME TO ATHEROSCLEROTIC PLAQUES AND METHODS OF USE

(75) Inventors: Erkki Ruoslahti, Buellton, CA (US); Juliana Hamzah, Santa Barbara, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 13/531,245

(22) Filed: Jun. 22, 2012

(65) Prior Publication Data
US 2013/0115167 A1 May 9, 2013

Related U.S. Application Data

(60) Provisional application No. 61/501,122, filed on Jun. 24, 2011.

(51) Int. Cl.
| | | |
|---|---|---|
| *A61K 49/00* | (2006.01) | |
| *A61K 38/08* | (2006.01) | |
| *A61K 51/08* | (2006.01) | |
| A61K 38/16 | (2006.01) | |
| A61K 38/03 | (2006.01) | |

(52) U.S. Cl.
CPC ............... *A61K 51/08* (2013.01); *A61K 38/08* (2013.01); *A61K 38/16* (2013.01); *A61K 38/03* (2013.01); *A61K 49/00* (2013.01); *A61K 49/005* (2013.01)

(58) Field of Classification Search
CPC ... A61K 51/08; A61K 38/16; A61K 49/0005; A61K 38/03; A61K 38/08; B23C 2210/02; B23C 2210/03; B23C 2240/32; B23C 5/10; B23C 5/28
See application file for complete search history.

(56) References Cited

U.S. PATENT DOCUMENTS

2007/0258889 A1* 11/2007 Douglas et al. ............... 424/1.37
2008/0014143 A1* 1/2008 Ruoslahti et al. ............. 424/9.1

OTHER PUBLICATIONS

Masaki Uchida, Protein Cage Nanoparticles Bearing the Lyp-1 peptide for Enhanced Imaging of Macrophage-Rich Vascular Lesions, ACS Nano, 2011, 5(4):2493-2502.*
Qingbo Xu, Mouse Models of Arteriosclerosis, American Journal of Pathology, vol. 165, No. 1, Jul. 2004.*
Agemy et al., Blood 116:2847-2856 (2010).
Briley-Saebo et al., J. Am. Call. Cardial. 57:337-347 (2011).
Dedio et al., J. Immunol. 160:3534-3542 (1998).
Fogal et al., Cancer Res. 68:7210-7218 (2008).
Fogal et al., Mol. Cell. Biol. 30:1303-1318 (2010).
Hamzah et al., "Specific penetration and accumulation of a homing peptide within atherosclerotic plaques of apolipoprotein E-deficient mice," PNAS, vol. 108, No. 17, pp. 7154-7159 (Apr. 26, 2011).
Laakkonen et al., Proc. Natl. Acad. Sci. USA 101:9381-9386 (2004).
Muta et al., J. Biol. Chem. 272:24363-24370 (1997).
Nahrendorf et al., Circulation 117:379-387 (2008).
Nahrendorf, et al., Circulation 114:1504-1511 (2006).
Park et al., Proc. Natl. Acad. Sci. USA 107:981-986 (2010).
Peters et al., Proc. Natl. Acad. Sci. USA 106:9815-9819 (2009).
Simberg et al., Proc. Natl. Acad.Sci. USA 104:932-936 (2007).
Zhang et al., Cancer Res. 66:5696-5706 (2006).

* cited by examiner

*Primary Examiner* — James H Alstrum Acevedo
*Assistant Examiner* — Erinne Dabkowski
(74) *Attorney, Agent, or Firm* — Jenkins, Wilson, Taylor & Hunt, P.A.

(57) ABSTRACT

Methods of targeting atherosclerotic plaques using LyP-1 related peptides are provided. In some embodiments, the methods include administering a peptide comprising a LyP peptide to an animal, wherein the peptide homes to an atherosclerotic plaque, thereby targeting the atherosclerotic plaque. Also provided are methods for ameliorating a sign or symptom associated with an inflammatory condition using LyP-1 related peptides.

8 Claims, 24 Drawing Sheets
(22 of 24 Drawing Sheet(s) Filed in Color)

Figure 1
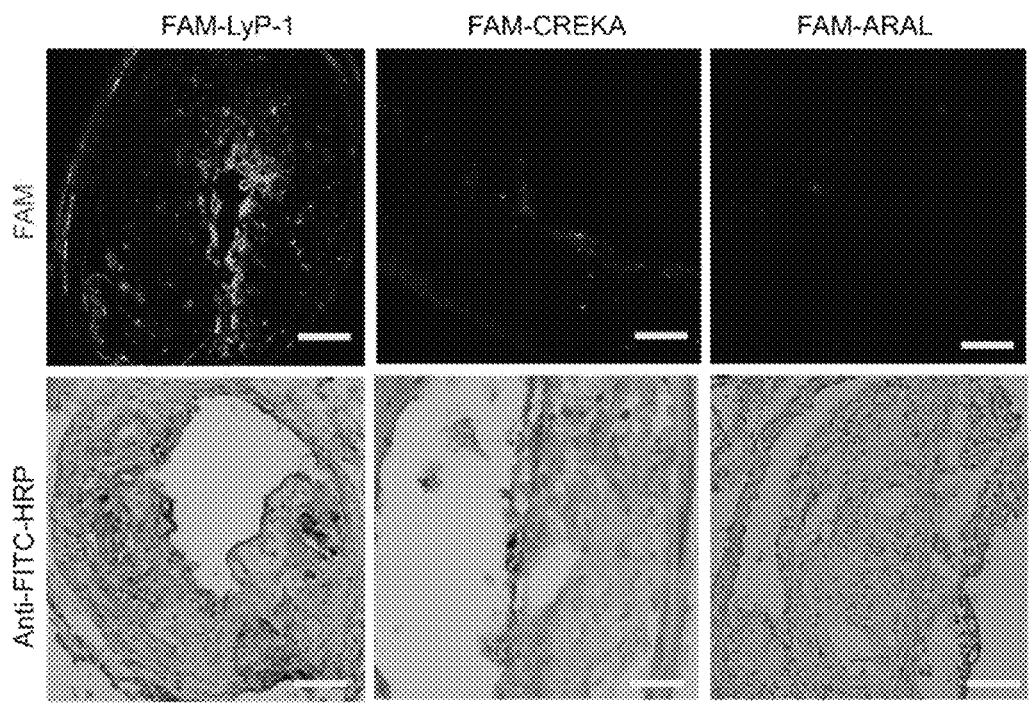
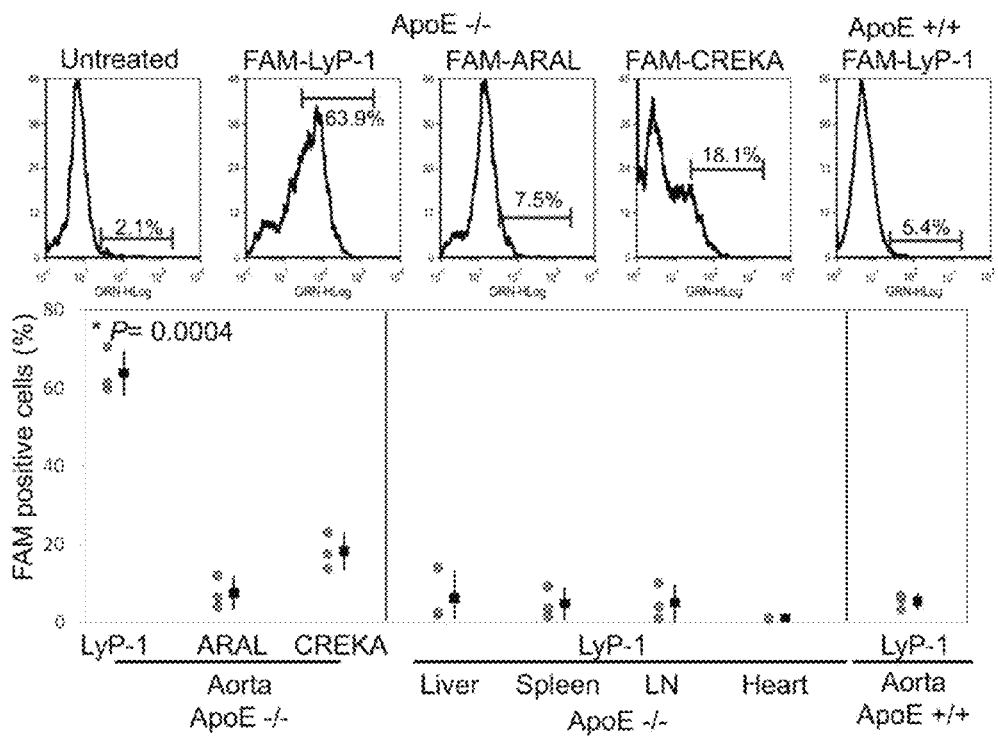

Figure 2
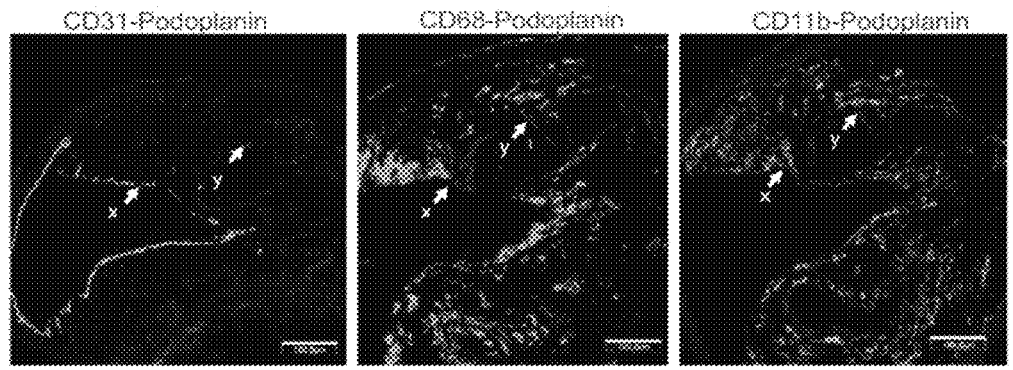
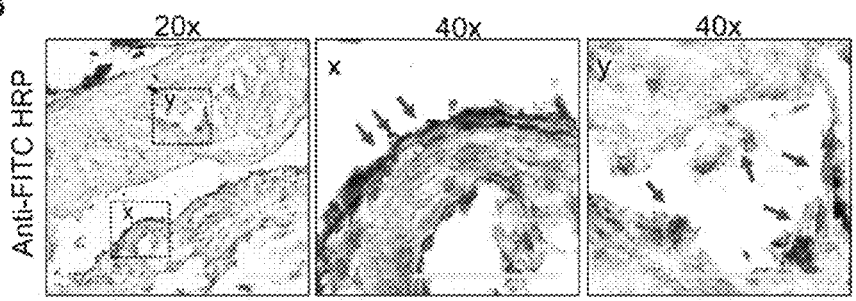
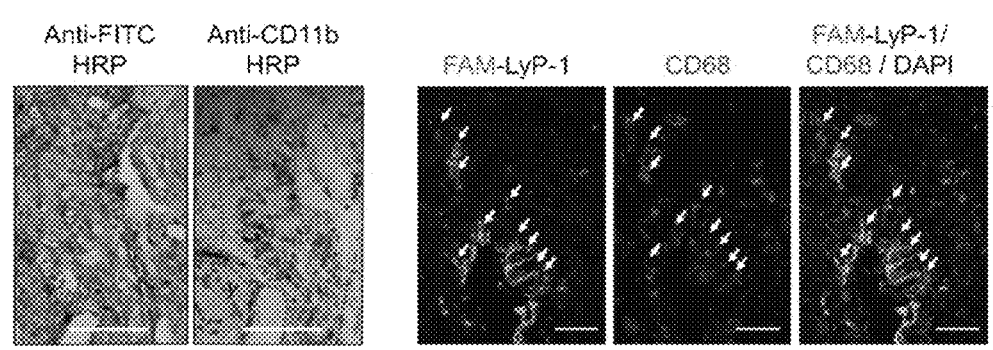
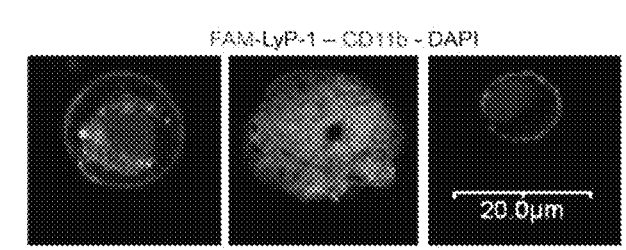
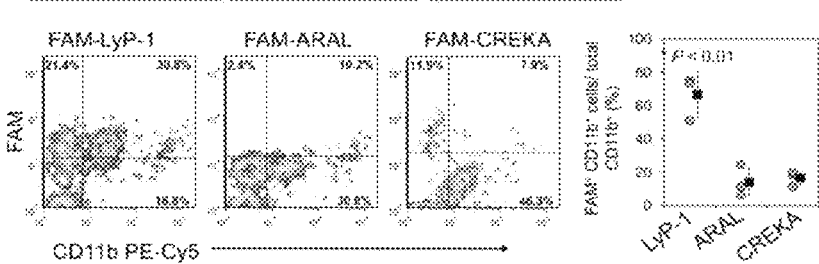

Figure 4
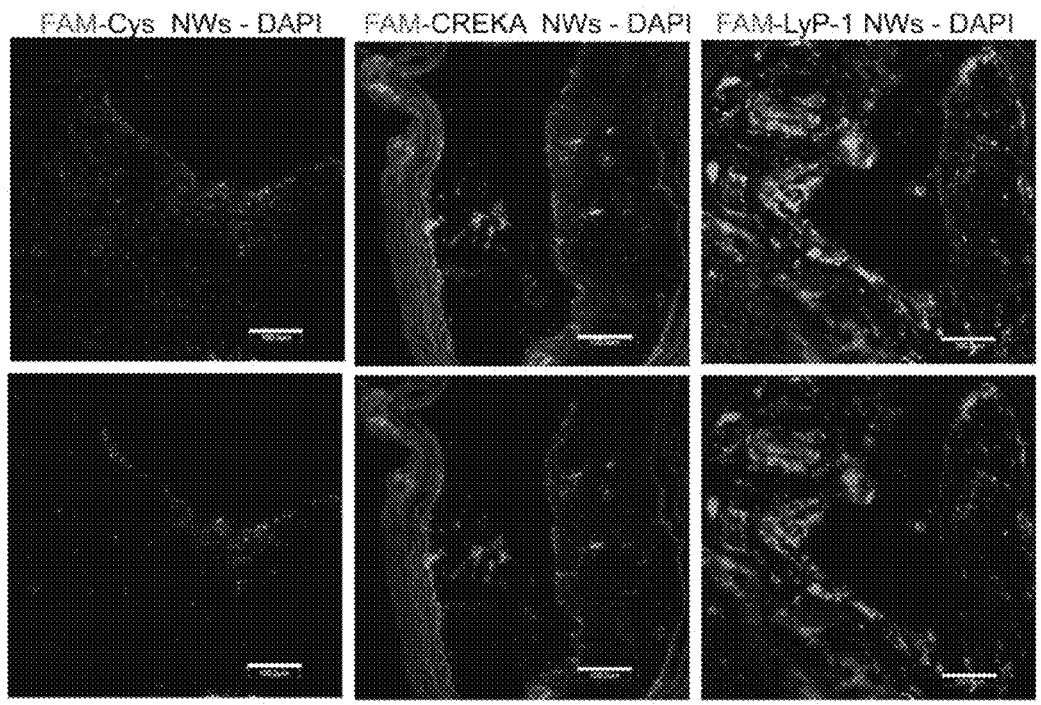
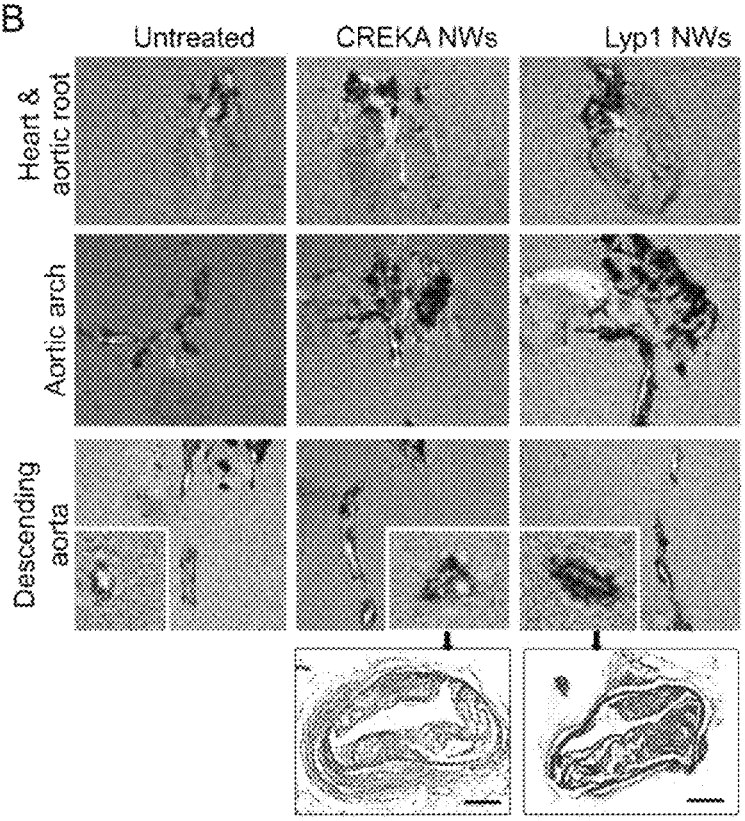
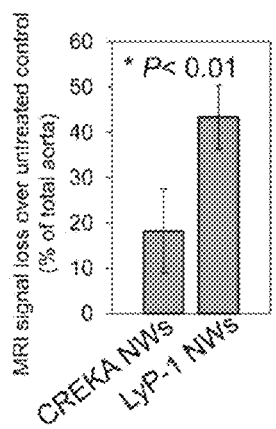

Figure 5
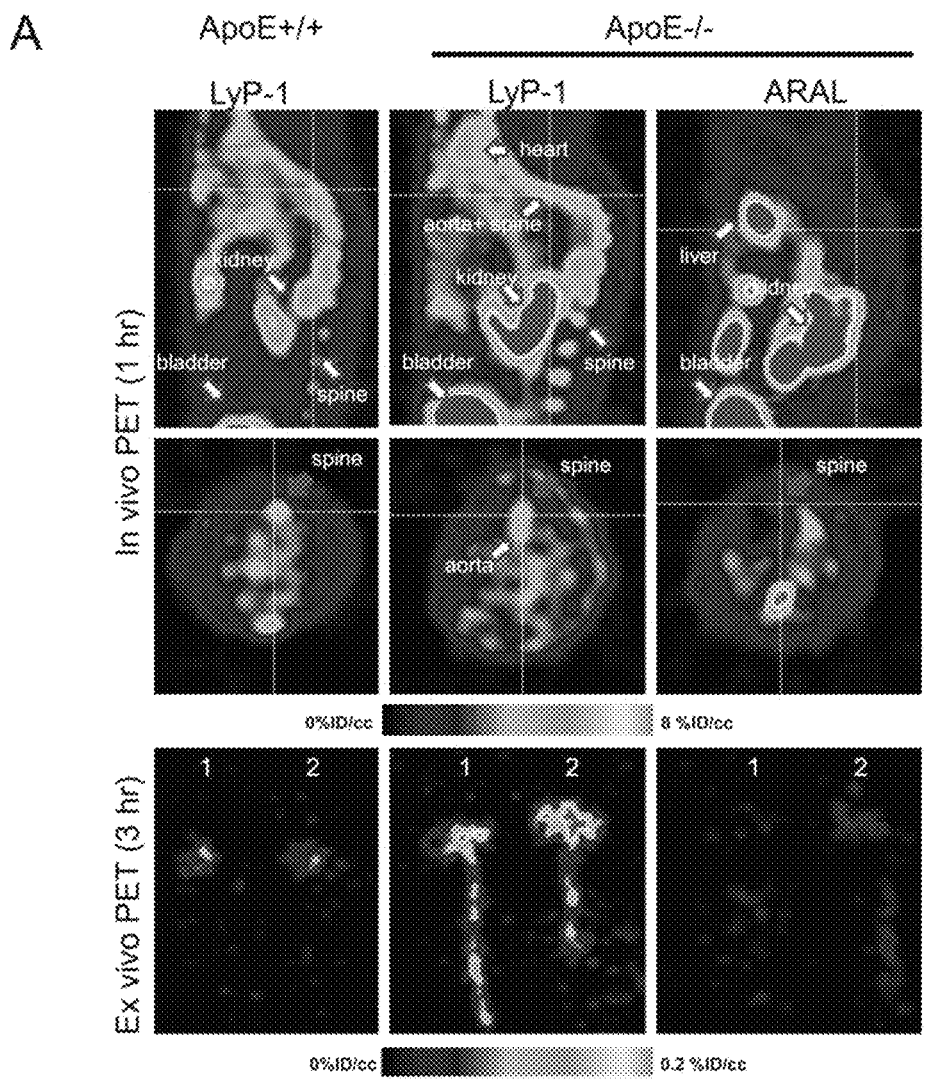
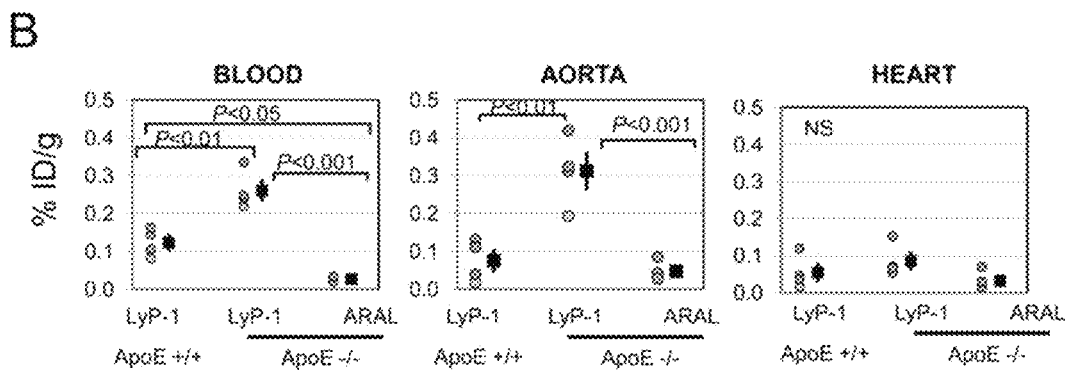

Figure 9
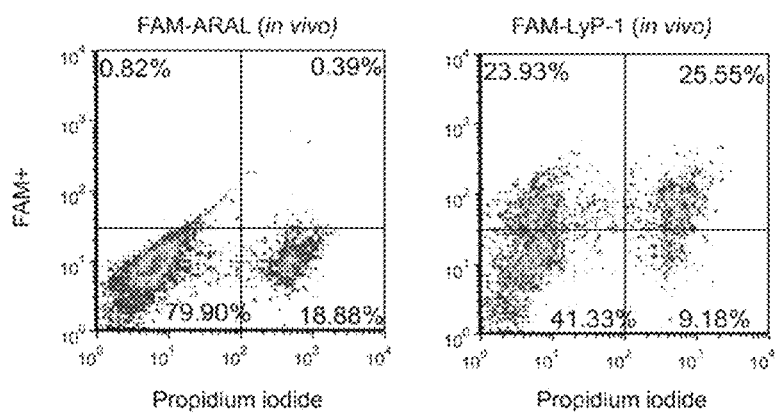
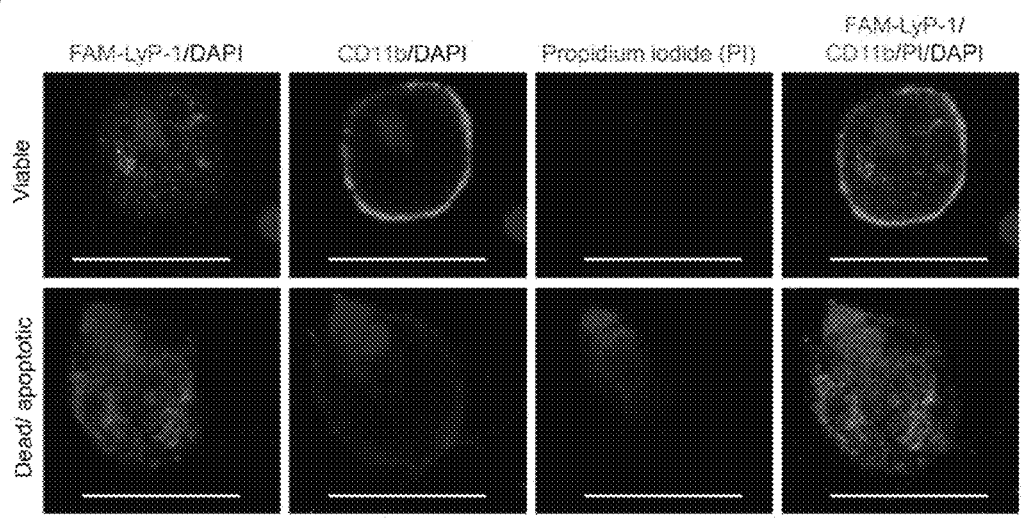

Figure 11
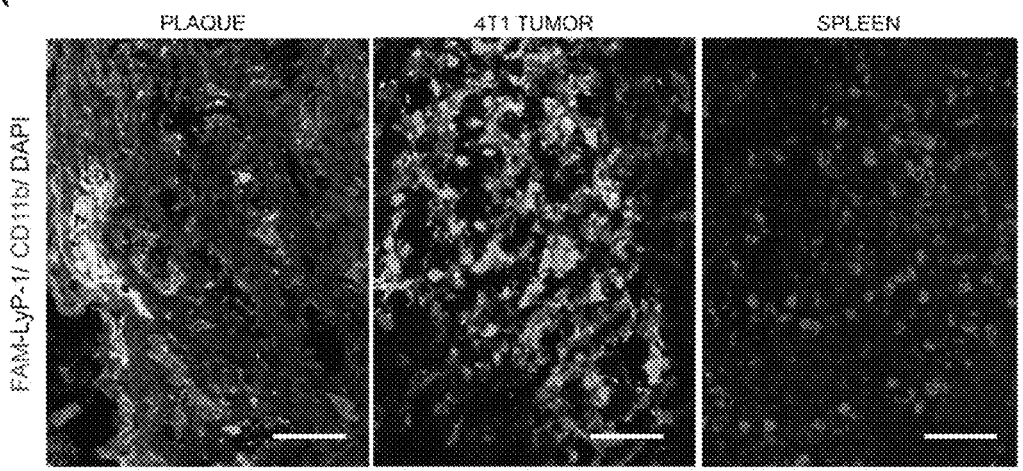
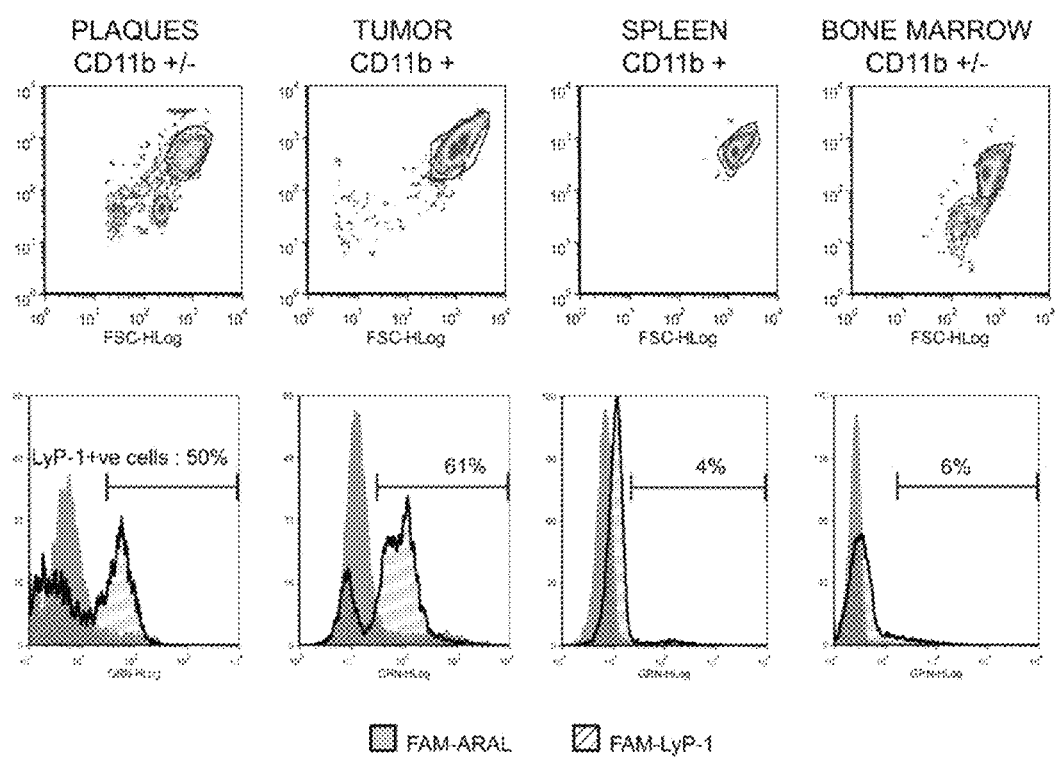

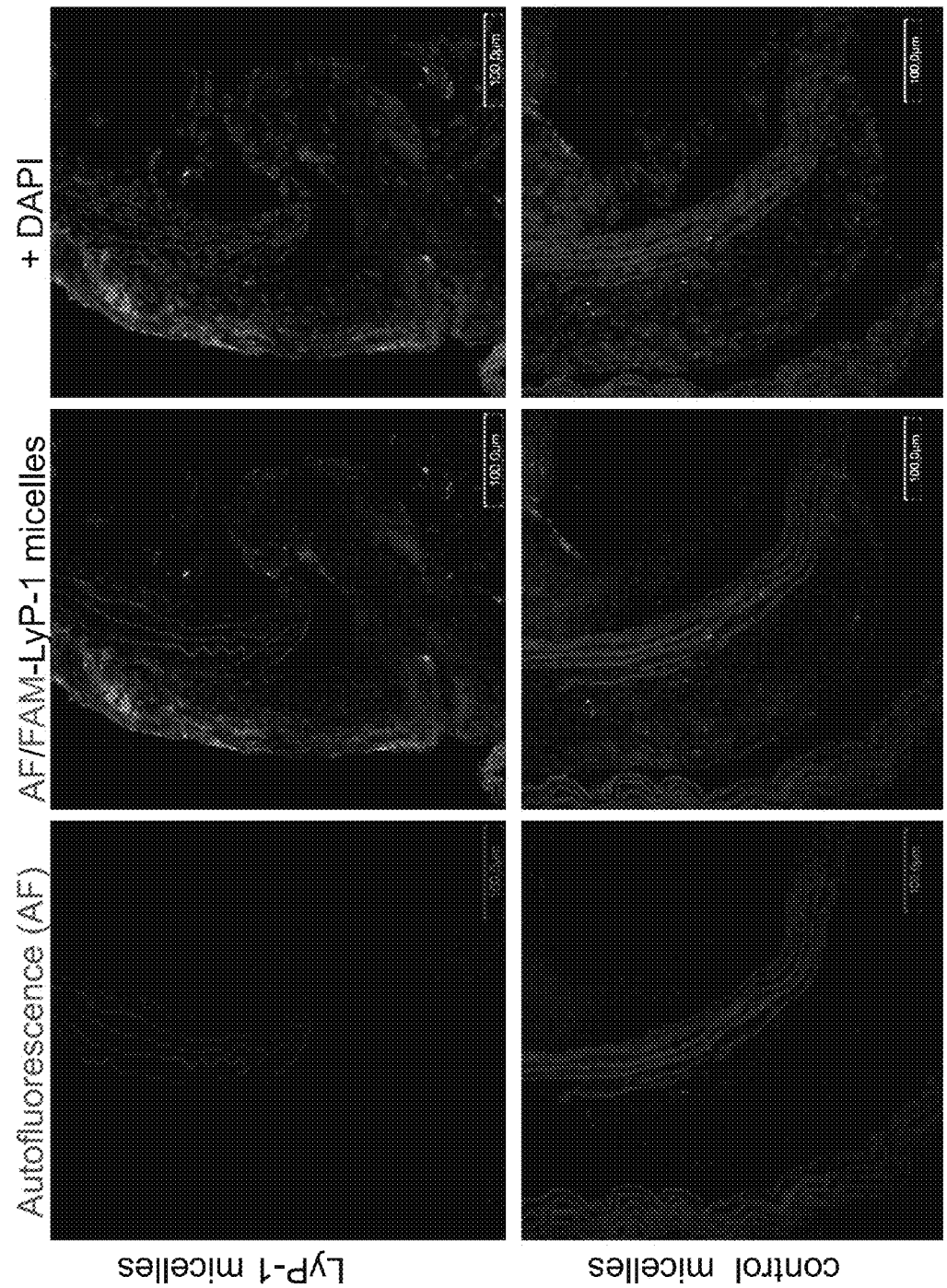

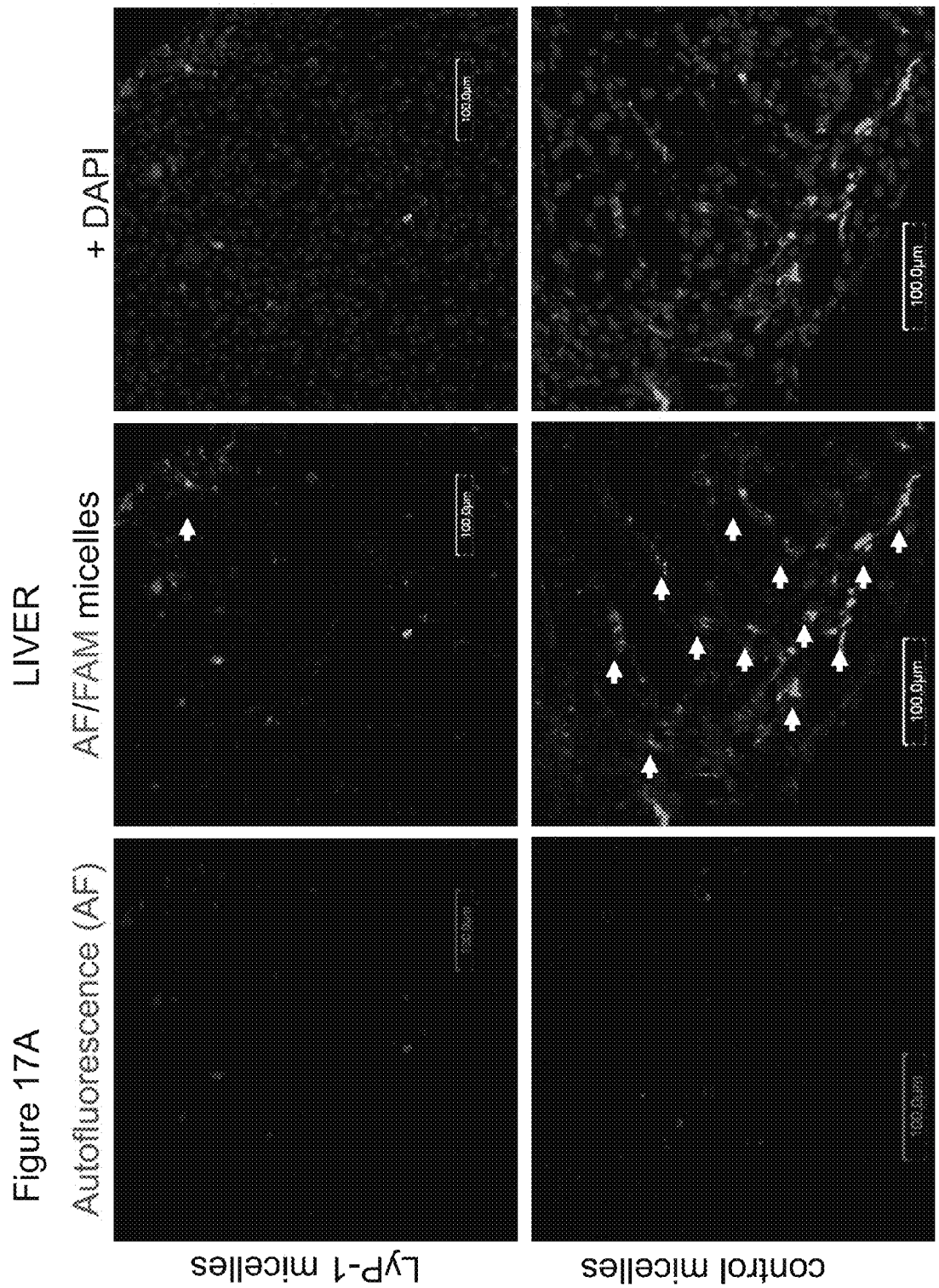

Figure 18
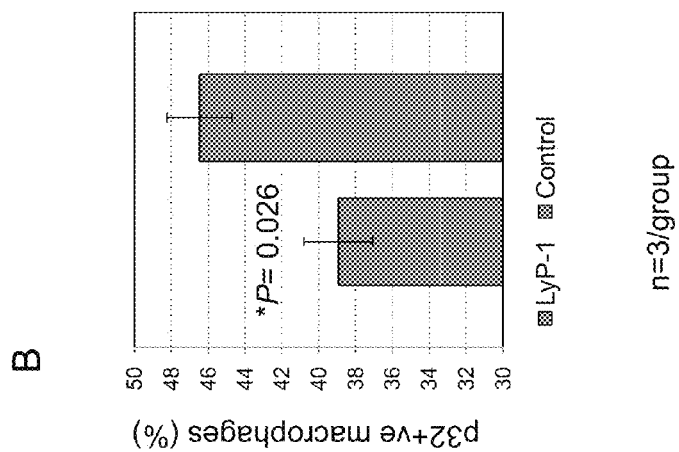
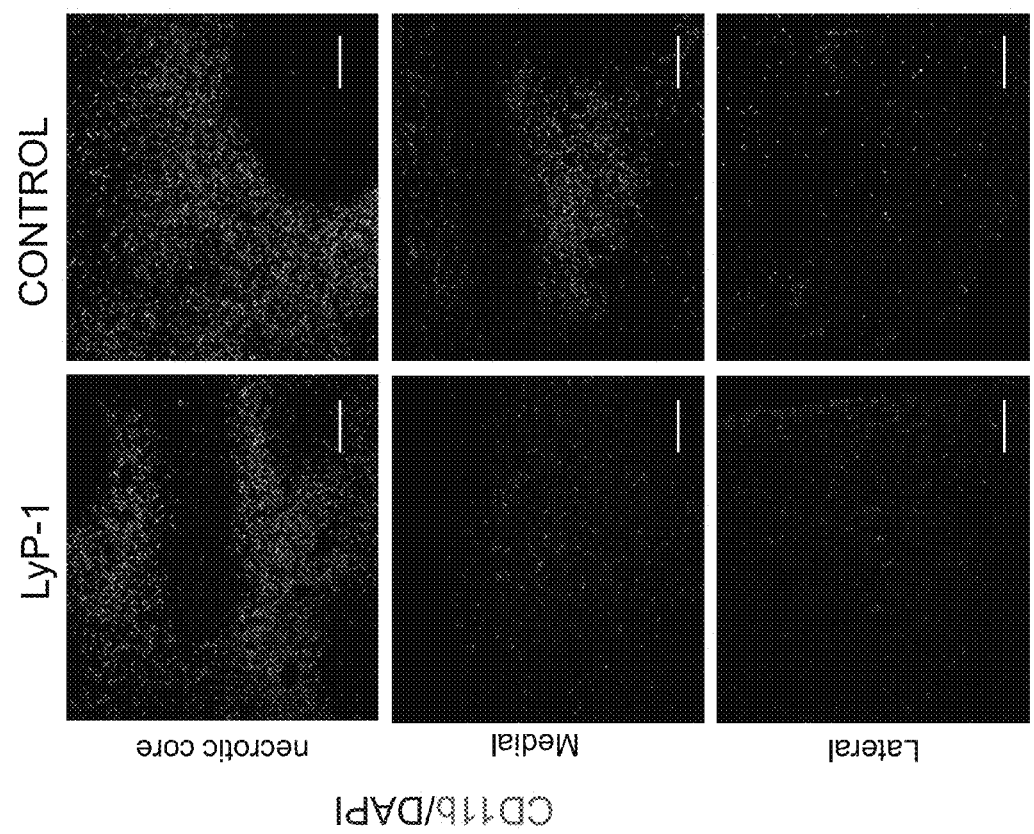

PEPTIDES THAT HOME TO ATHEROSCLEROTIC PLAQUES AND METHODS OF USE

This application claims the benefit of priority of U.S. Provisional application Ser. No. 61/501,122, filed Jun. 24, 2011, the entire contents of which are incorporated herein by reference.

Incorporated herein by reference is the Sequence Listing being submitted via EFS-Web as an ASCII text file named 12968-125-999_Sequence_Listing.TXT, created Aug. 27, 2012, and being 8,149 bytes in size.

This invention was made with government support under grant number 5 U01 HL080718 awarded by the National Heart Lung and Blood Institute of the National Institutes of Health. The government has certain rights in the invention.

BACKGROUND OF THE INVENTION

The present invention relates generally to homing peptides, and more specifically to peptides that home to atherosclerotic plaques and have anti-inflammatory activity.

The diagnosis and treatment of atherosclerosis is dominated by the detection of arterial occlusions, reversal of these occlusions by physical intervention, and long-term management of lipid metabolism. Much less effort has been directed to developing reagents that can specifically target the cellular and molecular components of atherosclerotic lesions. Yet such reagents could be valuable in specifically delivering imaging agents and therapeutics directly into plaques. Targeted delivery that uses carrier molecules with specific affinity for the target tissue (synaphic targeting) increases the efficacy of the targeted drug, while also reducing side effects.

Thus, there exists a need for reagents that target atherosclerotic plaques. The present invention satisfies this need and provides related advantages as well.

SUMMARY OF INVENTION

The invention provides methods of targeting atherosclerotic plaques using LyP-1 related peptides. The invention additionally provides methods of treating an inflammatory condition using LyP-1 related peptides.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B show peptide homing to atherosclerotic plaques. Atherosclerotic mice were injected with 100 μg of FAM-LyP-1 and the probe was allowed to circulate for 1 hour, after which the aorta was collected and the peptide was detected in tissue sections by fluorescence detection and staining with anti-FITC-HRP antibodies (brown). FIG. 1A shows in the upper panels a cross-section of aorta showing FAM-LyP-1 within plaque tissue. Only minimal fluorescence is observed in plaques from mice injected with FAM-CREKA (SEQ ID NO:4) and FAM ARAL (SEQ ID NO:5). The lower panels show a representative image (n=5 mice per group) of immunoperoxidase staining with an anti-FITC-HRP antibody showing LyP-1 accumulation in the plaque interior. Original magnification ×20. Scale bars, 100 μm. FIG. 1B shows flow cytometry analysis of cells released from plaques. The histograms in the upper panels indicate the number of FAM positive cells released from plaques after 4 hours in vivo circulation. A high percentage of cells containing LyP-1 fluorescence is observed. The FAM-LyP-1 uptake by plaque cells was significantly greater than the uptake of CREKA (SEQ ID NO:4), or the control peptide, ARAL (SEQ ID NO:5); LyP-1 is not seen the aorta in normal mice (ApoE+/+). (*P=0.0004 LyP-1 versus FAM-CREKA (SEQ ID NO:4) n=3 mice per group).

FIGS. 2A-2E show LyP-1 accumulation in atherosclerotic plaques and association with the aortic endothelium, lymphatics and macrophages. FIG. 2A shows identification of the luminal endothelium (anti-CD31, green, x), lymphatics (anti-podoplanin, red, y) and macrophages (anti-CD68 or anti-CD11b, green) in aorta sections. Original magnification ×20. Scale bars, 100 μm. In FIG. 2B, LyP-1 is seen at the luminal endothelium (arrow x) and in the lymphatics (arrow y). Original magnification, x20 and x40. Scale bars, 100 and 50 μm. FIG. 2C shows LyP-1 accumulation in macrophage-rich areas in the plaque interior. The right panels show FAM-LyP-1 localization in areas positive for the CD68 macrophage marker (red). The arrows point at cells expressing CD68 marker that were also positive for LyP-1 homing. Original magnification, x40. Scale bars, 100 μm (left) and 50 μm (right). FIG. 2D shows fluorescence microscopy analysis of cells released from plaque after 4 hours of circulation. FAM-LyP-1 (green) is present in both CD11b-positive (left panel; red) and CD11b-negative (middle panel) cells. Some CD11b-positive cells do not contain LyP-1 (right panel). FIG. 2E shows FACS analysis of the uptake of FAM-LyP-1, FAM-ARAL (SEQ ID NO:5) and FAM-CREKA (SEQ ID NO:4) by CD11b-positive plaque cells. More than half of the CD11b-positive cells were positive for LyP-1 uptake, whereas CREKA (SEQ ID NO:4) was taken up by a small number of CD11b-negative cells (P=0.0038).

FIG. 3A shows a representative confocal microscopy image showing that plaques are strongly positive for cell-surface p32 (ApoE−/−; red), whereas normal aorta (ApoE+/+) shows no staining. The blood vessels and parenchymal tissue of the major organs (shown for the liver and spleen) were also negative (original magnification, 40×; scale bars, 10 μm). FIG. 3B shows that a comparison of p32 staining in plaques and the spleen with and without permeabilization indicates cell surface p32 expression in the plaques, but not in the spleen (original magnification, x40; scale bars, 50 μm). FIG. 3C shows that FACS histograms show that one third of cells released from plaques were positive for cell surface p32 expression, whereas there was only a minor shift of the fluorescence intensity when the liver and spleen cells were stained for p32. FIG. 3D shows that a comparison of FAM-LyP-1 homing and p32 expression (red) indicates LyP-1 co-localizes in the same region that expressed p32. Squares: regions in the plaque where LyP-1 homing co-localized with p32 staining (original magnification, x20; scale bars, 100 μm).

FIGS. 4A-4C show that LyP-1 targeted nanoparticles (NWs) home to the interior of plaques. FAM-LyP-1 and FAM-CREKA (SEQ ID NO:4) NWs were intravenously (retro-orbital) injected in ApoE-null mice under isoflurane inhalation at a dose of 5 mg/kg body weight and allowed to circulate for 6 hours. FIG. 4A shows that histological analysis (FAM) shows minimal binding of non-targeted control NWs to the surface of plaques, whereas CREKA-targeted (SEQ ID NO:4) NWs show more accumulation on surface of plaques, and LyP-1-targeted NWs accumulate in the plaque interior. Original magnification, ×20. Scale bars, 100 μm. FIG. 4B shows ex vivo magnetic resonance (MR) imaging of plaque. Shown are representative images from untreated mice and mice injected with CREKA (SEQ ID NO:4) NWs and LyP-1-NWs (n=3-4 per group), depicting the heart, aortic root, aortic arch and descending aorta in axial and coronal planes. The axial slices show large plaque burden comparable to the hematoxylin and eosin histology of respective cross-sections of the aorta. Scale bars, 200 µm. FIG. 4C shows that LyP-1 NWs show a 42% decrease in T2* image amplitude compared with the untreated aorta (P<0.01 by Tukey's Comparison).

FIGS. 5A and 5B show microPET image and biodistribution analyses of atherosclerotic plaques targeted with LyP-1 labeled with [$^{18}$F]FBA. FIG. 5A shows sagittal (top row) and transverse (middle row), maximum intensity projection (MIPs) in vivo PET images of [$^{18}$F]FBA radiotracer coupled to LyP-1 and control ARAL (SEQ ID NO:5) an hour after intravenous injection in wild type ApoE+/+(for LyP-1 only) and in ApoE−/− (plaques) mice. The images showed overall tissue distribution (% ID/cc), of the peptide; distribution of [$^{18}$F]FBA-LyP-1 is detected within the aortic region, spinal region and in clearance organs (kidneys and bladder) during 1 hour circulation. Control peptide [$^{18}$F]FBA-ARAL (SEQ ID NO:5) shows widespread distribution in other organs. The bottom shows that MIP images of ex vivo aortas indicate greater accumulation throughout the aortic arch, roots and descending region in aortas containing plaques after injection with radiolabeled LyP-1. FIG. 5B shows biodistribution analysis of radioactivity (% ID/g) in blood, aorta and heart after 3 hour circulation. Circle; % ID/g from each mouse, square; mean % ID/g±SE for each group (n=4 per group). Data show at least 4-fold higher activity of [$^{18}$F]FBA LyP-1 in aortas containing plaques than in the normal aortas and in [$^{18}$F]FBA ARAL (SEQ ID NO:5) injected aortas (P<0.005). [$^{18}$F]FBALyP-1 also has higher blood retention when compared to [$^{18}$F]FBA-ARAL (SEQ ID NO:5) (P<0.005) but limited traces in the heart (no significant difference in % ID/g of between the three groups).

FIGS. 9A and 9B show that LyP-1 accumulates intracellularly in plaque macrophages. FIG. 9A shows FACS analysis of viable and dead cells (positive for propidium iodide, PI, staining) released from aorta that have taken up LyP-1 (FAM-positive cells) during the 3 hours after intravenous injection of FAM-LyP-1, showed almost 50% of the cells were still viable and unaffected by the tissue digestion procedure. FIG. 9B shows confocal microscopy images of viable (CD11b positive/PI negative) and dead (CD11b positive/PI positive) macrophages that showed LyP-1 internalization. Original magnification, ×40. Scale bars, 20 µm.

FIGS. 11A and 11B show that LyP-1 selectively binds to inflammatory associated macrophages known to express p32 on cell surface. FIG. 11A shows co-localization of FAM-LyP-1 in vivo in CD11b-positive cells in plaques and murine carcinoma, 4T1 tumors, but the CD11b positive cells in the spleen were negative of LyP-1 uptake after intravenous injection of FAM-LyP-1. FIG. 11B shows that FACS analysis indicates LyP-1 binds in vitro compared to ARAL (SEQ ID NO:5) only to primary cells released from plaques and isolated macrophages from 4T1 tumors. Macrophages isolated from the spleen and bone marrow cells did not show binding when directly incubated with LyP-1.

FIG. 14A shows dissected aorta attached to the spine. The white color of the plaques distinguishes them from the normal vessel wall. In FIG. 14B, the upper panel shows macroscopic appearance of dissected aortic and spinal tissue. The lower panel shows FAM-LyP-1 fluorescence in the dissected tissues shown in the upper panel; the aorta gives a strong signal, and a weaker signal is recorded from the spine. FIG. 14C shows immunoperoxidase staining of a transverse section of a vertebra with a peroxidase (HRP)-labeled anti-FITC antibody. Some FAM-LyP-1 accumulation is seen. Original magnification, ×10. Scale bars, 200 µm. FIG. 14D shows comparison of anti-FITC staining in the spine (expanded images from the boxed areas FIG. 14C) and in plaques. These representative images indicate widespread accumulation of FAM-LyP-1 in plaques and localized, low level accumulation in the spine (arrow). Original magnification, ×20. Scale bars, 100 µm.

FIG. 16 shows homing of LyP-1 micelles to atherosclerotic plaques. Atherosclerotic mice ApoE null mice kept on a high-fat diet) were intravenously injected with 200 µL of 1 mM FAM-LyP-1 or control micelles. Three hours later, the aorta was collected and sectioned (7 µm) and fluorescence (green) from the FAM-LyP-1 (upper panels) and control (lower panels) micelles was detected in the sections. Autofluorescence signal was detected in the red channel and nuclei were stained with DAPI (blue). The LyP-1 micelles were detected in the plaques, whereas only minimal fluorescence is observed in plaques from mice injected with the control micelles. Original magnification ×20. Scale bars, 100 µm.

FIGS. 17A and 17B show low non-specific uptake of LyP-1 micelles in the liver and spleen. Mice were injected with FAM-LyP-1 (upper panels) and control (lower panels) micelles as in FIG. 16, and fluorescence (green) was assessed in liver (FIG. 17A) and spleen (FIG. 17B) sections (7 µm). Autofluorescence signal was detected in the red channel and nuclei were stained with DAPI (blue). The control micelles showed stronger accumulation in the liver (arrows) than the LyP-1 micelles. Original magnification ×20. Scale bars, 100 µm.

FIGS. 18A and 18 B show treatment of tumor mice with LyP-1 peptide and the effect on tumor macrophages. To produce 4T1 breast cancer tumors, normal female BALB/c mice were orthotopically injected into the mammary fat pad with 1×10⁶ 4T1 cells suspended in 100 µL of PBS. The mice were treated with daily tail vein injections of 60 µg of LyP-1 or control peptide (ARALPSQRSR; SEQ ID NO:6) for 12 days. In FIG. 18A, tumor sections were analyzed for CD11b-positive (CD11b+ve) cells (macrophages; green) within the necrotic core, and medial and lateral parts of the tumor. Original magnification x20. Scale bars, 100 µm. FIG. 18B shows the percentage of cells positive for cell surface expression of the LyP-1 receptor, p32, among CD11b-positive cells (macrophages) in treated 4T1 tumors. Cell suspensions were prepared from 4T1 tumors from mice treated with LyP-1 or the control peptide. The tumors were incubated for 1 hour at 37° C. in a tissue digestion cocktail containing 2 mg/mL Collagenase IV (Worthington Biochem Corp) and 1 mg/mL DNAse 1 (Sigma) in high glucose DMEM media (Gibco). The resulting cell suspension was passed through 70 µm nylon mesh cell strainer (BD), and the live cells were double stained for cell surface p32 (rabbit anti-mouse p32) and macrophages (rat anti-mouse CD11b, ebioscience) and analyzed by FACS. The results show that the total number of macrophages and macrophages positive for p32 is reduced in the LyP-1-treated mice.

FIG. 23 shows accumulation of FAM-LyP-2 (green, upper and lower panel) within plaque tissue (blue, DAPI nuclei staining) Original magnification ×20. Scale bars, 100 µm.

DETAILED DESCRIPTION OF THE INVENTION

Figure 3:
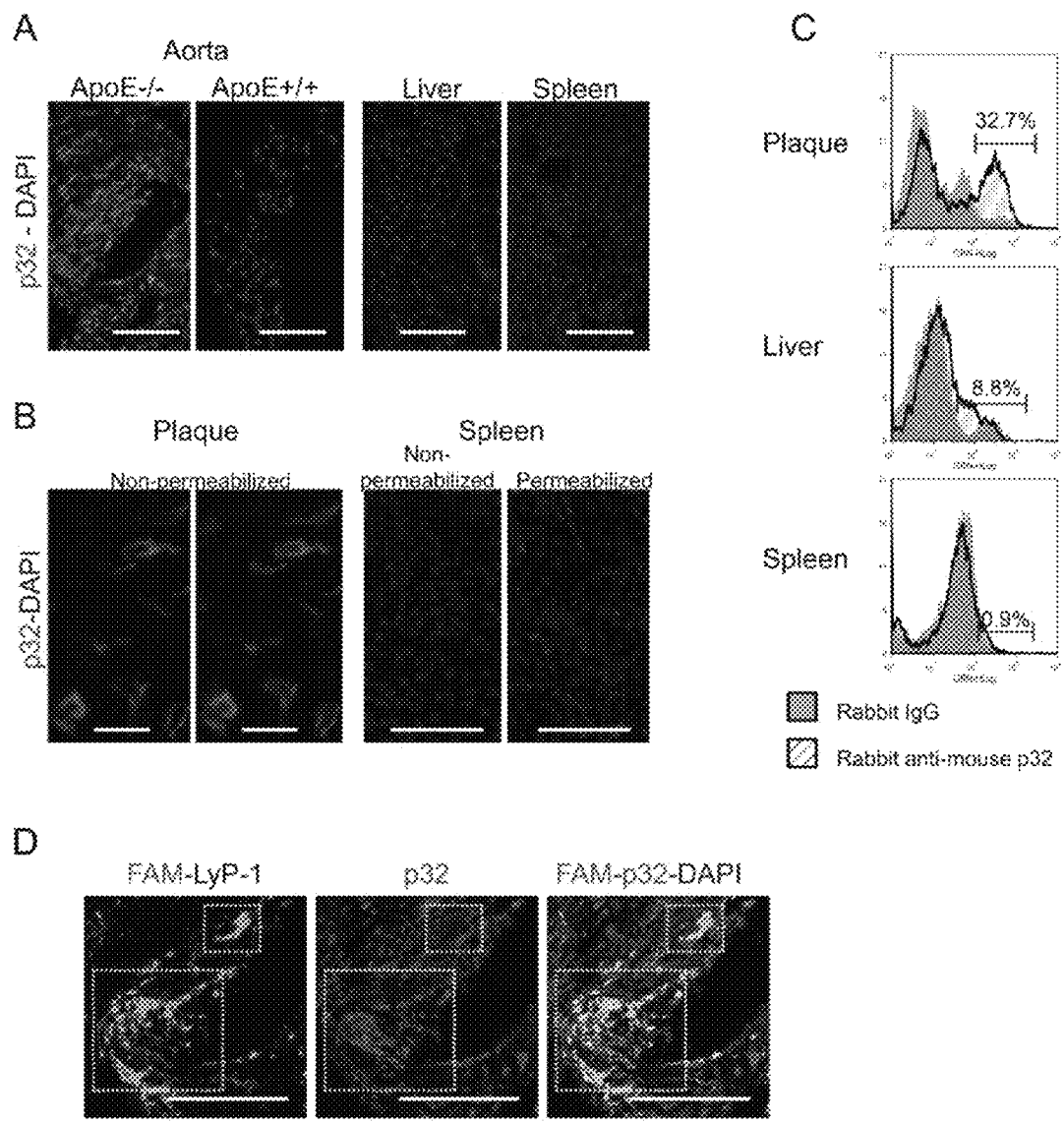
FIGS. 3A-3D show that plaques express cell surface p32.

The present invention is related to methods of targeting atherosclerotic plaques for diagnostic or therapeutic purposes. The invention also relates to the discover that the LyP-1 peptide has anti-inflammatory activity. The detection and management of atherosclerotic disease would greatly benefit from the ability to selectively deliver compounds into atherosclerotic plaques. As disclosed herein, such a delivery system can be based on a 9-amino acid cyclic peptide, LyP-1, or structurally and functionally related LyP peptides. LyP-1 was originally identified as a tumor-homing peptide characterized by targeting to tumor cells, tumor lymphatics, and tumor-associated macrophages (see also U.S. publication 2008/0014143).

As disclosed herein, the LyP-1 peptide targets atherosclerotic plaques (see Examples). Furthermore, the LyP-1 peptide penetrates into and accumulates deep within atherosclerotic plaques. Moreover, the LyP-1 peptide was additionally found to exhibit anti-inflammatory activity. Thus, the invention provides methods utilizing the atherosclerotic plaque targeting activity and/or anti-inflammatory activity of a LyP peptide such as LyP-1 or others described herein.

As disclosed herein, the ability of LyP-1 to home to atherosclerotic plaques was tested. LyP-1 was labeled with fluorescein and intravenously injected into ApoE-null mice that had been kept on a high-fat diet to induce atherosclerotic disease (Example I). LyP-1 accumulated in the interior of plaques, predominantly in macrophages. Analysis of cells released from the plaques showed that more than 60% of the cells were positive for LyP-1 fluorescence. Another plaque-homing peptide, CREKA (SEQ ID NO:4), which binds to fibrin-fibronectin clots and accumulates at the surface of the plaques, yielded fewer positive cells. Tissues that did not contain plaque yielded only traces of LyP-1-positive cells. LyP-1 was capable of delivering intravenously injected nanoparticles to plaques; abundant plaque accumulation of LyP-1-coated superparamagnetic iron oxide nanoparticles in the plaque interior was observed, whereas CREKA-NWs (SEQ ID NO:4) remained at the surface of the plaques. Intravenous injection of LyP-1 coupled to a 4-[$^{18}$F]fluorobenzoic acid ([$^{18}$F]FBA) radio-tracer indicated a four to six-fold increase in peak positron emission tomography (PET) activity in aortas containing plaques (0.31% ID/g) compared to aortas from normal mice injected with [$^{18}$F]FBA-LyP-1 (0.08% ID/g, P<0.01) or aortas from atherosclerotic ApoE mice injected with [$^{18}$F]FBA-labeled control peptide (0.05% ID/g, P<0.001). The results disclosed herein indicate that LyP-1 is an agent for the targeting atherosclerotic lesions.

Moreover, additionally disclosed herein is the discovery that LyP peptides such as the LyP-1 peptide has anti-inflammatory activity (see Example II). Thus, the invention additionally provides methods for treating an inflammatory condition by ameliorating a sign or symptom associated with an inflammatory condition.

The invention relates to LyP peptides, including but not limited to the LyP peptides disclosed herein. It understood that a LyP peptide has the structural and functional activity of a peptide such as LyP-1, which selectively homes to atherosclerotic plaques and exhibit anti-inflammatory activity. Exemplary LyP peptides include, but are not limited to, peptides comprising SEQ ID NOS:1, 2 or 3 or NXXTX, as discussed below. As used herein, the LyP-1 peptide refers to the sequence CGNKRTRGC (SEQ ID NO:1)(see also U.S. publication 2008/0014143, which is incorporated herein by reference). In one embodiment of the invention, the methods utilize a peptide comprising SEQ ID NO:1, or a peptidomimetic thereof. In another embodiment of the invention, the methods utilize a conjugate of peptide comprising SEQ ID NO:1 linked to a moiety. Another exemplary peptide useful in methods of the invention is a peptide comprising CNRRTKAGC (SEQ ID NO:2), also referred to as LyP-2 peptide (see Zhang et al., *Cancer Res.* 66:5696-5706 (2006). This peptide has been found to target atherosclerotic plaques similar to the LyP-1 peptide. Yet another exemplary peptide useful in methods of the invention is a peptide comprising CGNRRTK (SEQ ID NO:3), also referred to herein as tLyP-1. The invention provides a peptide comprising SEQ ID NO:3 as well as methods of the invention using this peptide. It is further understood that peptides having the structural characteristics of these exemplary peptides can function similarly in targeting atherosclerotic plaques and/or exhibiting anti-inflammatory activity and are considered to be LyP peptides. One such exemplary peptide is a peptide comprising the amino acid sequence NXXTX, where X is a basic amino acid such as Arg or Lys and where X can be independently selected from Arg or Lys, wherein the peptide targets atherosclerotic plaques and/or exhibits anti-inflammatory activity. It is understood that a peptide comprising NXXTX can have one or more amino acids on the N-terminus and/or C-terminus, including but not limited to C or CG on the N-terminus and/or GC or AGC on the C-terminus as in SEQ ID NOS:1-3.

In one embodiment, the invention provides a method of targeting an atherosclerotic plaque by administering a peptide comprising a LyP peptide, for example, SEQ ID NOS:1, 2 or 3 or NXXTX, to an animal, wherein the peptide homes to an atherosclerotic plaque, thereby targeting the atherosclerotic plaque. As disclosed herein, the LyP-1 peptide not only targets atherosclerotic plaques but also penetrates and accumulates within atherosclerotic plaques. Thus the invention additionally provide a method targeting an atherosclerotic plaque, wherein the peptide penetrates and accumulates within the atherosclerotic plaque.

In such a method of targeting an atherosclerotic plaque, the peptide can be provided in the form of a conjugate linked to a moiety. Thus, the methods can be utilized to target an atherosclerotic plaque and bring to the plaque a moiety such as a detectable moiety or a therapeutic moiety. For example, the methods of the invention can be utilized to target atherosclerotic plaques with a detectable moiety for diagnostic purposes that facilitate visualization of the atherosclerotic plaques, including visualization to facilitate administration of therapeutic agents at the site of the atherosclerotic lesion. Alternatively, the peptide can be utilized to target a therapeutic moiety to an atherosclerotic plaque by linking a therapeutic agent to a peptide comprising a LyP peptide, for example, SEQ ID NOS:1, 2 or 3 or NXXTX. Based on the atherosclerotic plaque targeting activity of the peptide, the methods can be used to deliver a therapeutic agent to an atherosclerotic plaque. In a particular embodiment, the therapeutic agent linked in a peptide conjugate and targeted to an atherosclerotic plaque can be a thrombolytic agent. Thus, the methods can be used to concentrate thrombolytic agents at the site of an atherosclerotic plaque.

The invention additionally provides a method of ameliorating a sign or symptom associated with an inflammatory condition by administering a peptide comprising a LyP peptide, for example, SEQ ID NOS:1, 2 or 3 or NXXTX, to an animal having an inflammatory condition, thereby ameliorating a sign or symptom associated with the inflammatory condition. An inflammatory condition can include those disclosed herein or well known to those skilled in the art, including, for example, atherosclerosis or dermatitis. As disclosed herein, an inflammatory reaction can occur as an acute response to tissue trauma cased by a microbial or viral infection, exposure to chemicals and/or physical insult or injury. Thus, a peptide comprising a LyP peptide, for example, SEQ ID NOS:1, 2 or 3 or NXXTX, can be used to treat an inflammatory condition associated with an infection by ameliorating a sign or symptom associated with the inflammatory response associated with the infection. In such a case, the methods are applied to an inflammatory condition associated with an infection where the inflammatory response is deleterious to the organism rather than beneficial, as when the inflammatory response functions to fight an infection. Since inflammatory responses to tissue trauma or infection are part of an organism's defense mechanisms to protect from the trauma or infection, the methods of the invention for ameliorating a sign or symptom associated with an inflammatory condition are particularly useful when applied to reduce the inflammatory response in an inflammatory condition for which reducing the inflammatory response is beneficial, including but not limited to the inflammatory conditions disclosed herein. One skilled in the art will readily recognize an effective amelioration of a sign or symptom associated with an inflammatory condition, including but not limited to a change in a sign or symptom associated with an inflammatory condition. One skilled in the art, depending on the inflammatory condition being treated, will understand suitable signs or symptoms associated with the condition that are suitable for determining whether a sign or symptom associated with the condition has been ameliorated. Such signs or symptoms include measurable criteria as well as a patient's description of an improvement in a sign or symptom associated with an inflammatory condition. For example, ameliorating a sign or symptom associated with an inflammatory condition includes measurably reducing the inflammatory response associated with the inflammatory condition. Such a reduction in an inflammatory response can be readily measured by those skilled in the art. Measurable criteria for determining the amelioration of a sign or symptom associated with an inflammatory condition, include, but are not limited, measuring an increase or decrease of a cell type associated with an inflammatory response, an increase or decrease in a signaling molecule such as a cytokine or other factors (interferon, tumor necrosis factor (TNF), granulocyte macrophage-colony stimulating factor (GM-CSF)) and the like, or any other effects known to those skilled in the art to be associated with an inflammatory response (see Examples and, for example, Nathan, *Nature* 420:846-852 (2002); Tracey, *Nature* 420: 853-859 (2002)).

The methods of the invention can utilize a conjugate of a peptide comprising a LyP peptide, where the LyP peptide is conjugated to a moiety. The moiety can be, for example, a detectable agent or therapeutic agent, as disclosed herein.

One skilled in the art will readily understand that various detectable agents can be used in a conjugate with a peptide comprising a LyP peptide. Exemplary detectable agents are disclosed herein. One skilled in the art further understands that any of a variety of therapeutic agents can be useful in the conjugates of the invention including, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. In a particular embodiment, a method of the invention utilizes a conjugate of a peptide comprising a LyP peptide linked to an anti-thrombotic agent or thrombolytic agent.

The term "homing peptide" or "homing peptidomimetic" means a peptide or peptidomimetic that selectively localizes in vivo to atherosclerotic plaques in preference to most other tissues and vasculature. The term "selectively homes," as used herein in reference to a molecule, means that, in vivo, the homing molecule localizes preferentially to atherosclerotic plaques as compared to most other tissues or vasculature. Selective homing generally is characterized by at least a two fold greater localization in atherosclerotic plaques as compared to other tissues such as brain, lung, kidney and muscle. A homing molecule can be characterized by 5 fold, 10 fold, 20 fold or more preferential localization to atherosclerotic plaques as compared to many or most tissues. It is understood that a homing molecule can home, in part, to vasculature or tissues outside of atherosclerotic plaques or to a small population of cells outside of atherosclerotic plaques in addition to selectively homing to atherosclerotic plaques.

As discussed above, a homing molecule specifically binds to atherosclerotic plaques. As used herein, the term "specifically binds" or "specifically binding" means binding that is measurably different from a non specific interaction. Specific binding can be measured, for example, by determining binding of a molecule compared to binding of a control molecule, which generally is a molecule of similar structure that does not have binding activity. Specific binding also can be indicated if the homing molecule has measurably higher affinity for cells expressing or transfected with gC1q/p32 (p32/gC1q-R), the receptor for LyP-1 peptide, than for cells that do not express the receptor. The measurably higher affinity can be, for example, an increase of at least 100-fold, 200-fold, 300-fold, 500-fold or more for cells transfected with the receptor as compared to control cells. Binding specificity also can be confirmed, for example, by competitive inhibition with a known receptor-binding molecule, for example, the LyP-1 peptide.

Furthermore, the term specifically binding, as used herein, encompasses both low and high affinity specific binding. Specific binding can be exhibited, for example, by a low affinity homing molecule having a Kd of at least about $10^{-4}$ M. Specific binding also can be exhibited by a high affinity homing molecule, for example, a homing molecule having a Kd of at least about $10^{-5}$ M. Such a molecule can have, for example, a Kd of at least about $10^{-6}$ M, at least about $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful and encompassed by the invention. Low affinity homing molecules can be useful in targeting, without limitation, multivalent conjugates including viruses and other particles. High affinity homing molecules are useful in targeting, without limitation, multivalent and univalent conjugates.

Also provided herein are multivalent conjugates, which incorporate at least two homing molecules that each selectively homes to atherosclerotic plaques. In particular embodiments, a multivalent conjugate of the invention includes at least ten or at least 100 of such homing molecules. A variety of therapeutic agents are useful in the multivalent conjugates of the invention including, but not limited to, phage and other therapeutic agents described further below. In one embodiment, the invention provides a multivalent conjugate containing at least two homing peptides or peptidomimetics that each selectively homes to atherosclerotic plaques, specifically binds p32/gC1q-R and/or exhibits anti-inflammatory activity. In another embodiment, such a conjugate contains at least ten homing peptides or peptidomimetics that each selectively homes to atherosclerotic plaques, specifically binds p32/gC1q-R and/or exhibits anti-inflammatory activity. In still another embodiment, a conjugate of the invention contains at least 100 homing peptides or peptidomimetics that each selectively homes to atherosclerotic plaques, specifically binds p32/gC1q-R and/or exhibits anti-inflammatory activity.

In specific embodiments, a multivalent conjugate of the invention includes 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 125 or more, 150 or more, 200 or more, 250 or more, 300 or more, 350 or more, 400 or more, 450 or more, 500 or more or even more homing molecules that selectively home to atherosclerotic plaques, specifically bind p32/gC1q-R and/or exhibit anti-inflammatory activity. In one embodiment, the homing molecules have an identical amino acid sequence. In a further embodiment, the multivalent conjugate includes homing molecules having non-identical amino acid sequences. For example, the multivalent conjugate can contain independently peptides comprising a LyP peptide, for example, SEQ ID NOS:1, 2 or 3 or NXXTX, and optionally being independently of varying lengths. Moieties useful in a multivalent conjugate of the invention that incorporates multiple homing molecules include, but are not limited to, phage; retroviruses; adenoviruses; adeno-associated viruses and other viruses; cells; liposomes; polymeric matrices; non-polymeric matrices or particles such as gold particles; microdevices; nanodevices; and nano scale semiconductor materials.

A multivalent conjugate of the invention can contain, for example, a liposome or other polymeric matrix linked to at least two homing molecules that each selectively homes to atherosclerotic plaques, specifically binds p32/gC1q-R and/or exhibits anti-inflammatory activity. If desired, the liposome or other polymeric matrix can be linked to at least 10, at least 20, at least 30, at least 100, and the like as disclosed herein, of such homing molecules. Homing molecules useful in such a multivalent conjugate can independently include, for example, an amino acid sequence consisting of or comprising a LyP peptide, for example, SEQ ID NOS:1, 2 or 3 or NXXTX. Additionally, a homing peptide can comprise a conservative variant or peptidomimetic of such a sequence, as disclosed herein. Liposomes composed, for example, of phospholipids or other lipids, are nontoxic, physiologically acceptable and metabolizable carriers that are relatively simple to make and administer (Gregoriadis, *Liposome Technology*, Vol. 1 (CRC Press, Boca Raton, Fla. (1984)). One skilled in the art understands that, in a multivalent conjugate of the invention, the liposome or other polymeric matrix additionally can include another component if desired such as, without limitation, a therapeutic agent, anti angiogenic agent, anti-inflammatory agent, immunosuppressive agent and the like.

Based on the identification of molecules that selectively home to atherosclerotic plaques, the present invention provides methods for directing a moiety to atherosclerotic plaques and methods of treating a disease or condition associated with atherosclerotic plaques, including but not limited to cardiovascular disease and/or stroke. The present invention provides, for example, methods of directing a moiety to atherosclerotic plaques in a subject by administering to the subject a conjugate containing a moiety linked to a homing molecule that selectively homes to atherosclerotic plaques, specifically binds p32/gC1q-R and/or exhibit anti-inflammatory activity, thereby directing the moiety to atherosclerotic plaques. In a method of the invention, a homing molecule can home to atherosclerotic plaques in vivo with a selectivity, for example, of at least 5-fold relative to non-recombinant phage or another negative control, and can be, for example, a homing peptide or peptidomimetic such as a peptide comprising a LyP peptide, for example, SEQ ID NOS:1, 2 or 3 or NXXTX. In one embodiment, a method of the invention for directing a moiety to atherosclerotic plaques relies on a homing peptide or peptidomimetic containing the amino acid sequence of a LyP peptide, for example, SEQ ID NOS:1, 2 or 3 or NXXTX, or a conservative variant or peptidomimetic thereof. A homing peptide or peptidomimetic useful in the invention may optionally be conformationally constrained. Furthermore, any of a variety of moieties can be useful in the methods of the invention including, without limitation, detectable moieties such as radionuclides and fluorescent molecules. Moieties useful in the invention further encompass, without limitation, therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. In a particular embodiment, the therapeutic agent is an thrombolytic agent.

As discussed further herein, the, peptides, conjugates and methods of the invention can be useful for treating any of a variety of diseases associated with the formation of atherosclerotic plaques, including but not limited to, cardiovascular diseases and/or stroke. In addition, the LyP-1 peptide has been found to itself have anti-inflammatory activity. Thus, additionally provided are peptides comprising a LyP peptide, for example, SEQ ID NOS:1, 2 or 3 or NXXTX, or peptidomimetics thereof, and methods for treating inflammatory conditions, including infections and diseases associated with inflammation, that is, inflammatory diseases or disorders. Exemplary inflammatory diseases or disorders are described herein. The methods of the invention can be used to treat acute inflammatory conditions, such as an inflammatory reaction to a microbial infection, or chronic inflammatory conditions, such as those disclosed herein that result in inflammatory disorders or diseases.

Inflammation is the response of an organism's immune system to the damage caused to its cells and vascularized tissues by microbial pathogens such as viruses, bacteria or parasites or by injurious chemicals or physical insults. Inflammation is therefore a protective reaction to a potential insult to the organism. In some instances, however, an inflammatory response can be exhibited in a chronic state, resulting in diseases such as arthritis, multiple sclerosis, cancer, and autoimmune diseases.

As used herein, an "inflammatory condition" refers to a condition in which an inflammatory response occurs, including acute and chronic inflammatory responses. In the methods disclosed herein, it is understood by those skilled in the art that methods of ameliorating a sign or symptom associated with an inflammatory condition refers to an inflammatory condition in which it is desirable to reduce an inflammatory response. This is in contrast to an inflammatory response that is part of the immune response of an organism such as an inflammatory response to a pathogen, or a chemical or physical insult, where the inflammatory response provides a beneficial effect to the organism. It is understood by those skilled in the art that numerous conditions include an inflammatory component and are included within the meaning of an "inflammatory condition." The term "anti-inflammatory" is understood to mean reducing inflammation. Therefore, the anti-inflammatory activity of the peptides disclosed herein refers to the activity of reducing inflammation, as measured by any of the well known characteristics of an inflammatory response. Ameliorating a sign or symptom associated with an inflammatory condition includes anti-inflammatory activity such as reducing inflammation.

Numerous diseases and disorders are associated with an inflammatory response and therefore have an inflammatory component. For example, inflammation is known to play a role in the progression of some types of atherosclerosis (Libby, *Nature* 420:868-874 (2002)), cancer (Coussens and Werb, *Nature* 420:860-867 (2002)), autoimmune diseases (Benoist and Mathis, *Nature* 420:875-878 (2002), and sepsis (Cohen, *Nature* 420:885-891 (2002)). Inflammatory disorders include, but are not limited to, Alzheimer's disease, anaphylaxis, anklyosing spondylitis, asthma, atherosclerosis, dermatitis, including atopic dermatitis, chronic obstructive pulmonary disease, Crohn's disease (regional enteritis), gout, Hashimoto's disease, ischemia-repurfusion injury, including occlusive and embolic stroke and myocardial infarction, multiple sclerosis, osteoarthritis, pemphigus, periodic fever syndrome, psoriasis, rheumatoid arthritis, sarcoidosis, system lupus erythematosus, type I diabetes mellitus, ulcerative colitis, vasculitides, including Wegener's syndrome, Goodpasture's syndrome, giant cell arteritis, and polyarteritis nodosa, and xenograft/transplant rejection (Nathan, *Nature* 420:846-852 (2002)). Infectious diseases can result in inflammatory responses that contribute to pathology in addition to the infectious agent. Such infectious disease include, but are not limited to, bacterial dysentery, Chagas disease (*Trypanosoma cruzi*), cystic fibrosis pneumonitis, filariasis, *Helicobacter pylori* gastritis, hepatitis C, influenza virus pneumonia, leprosy (tubercuoloid form), Neisserial or pneumococcal meningitis, post-streptococcal glomerulonephritis, sepsis syndrome, tuberculosis and malaria (*Plasmodium falciparum*). Additional diseases in which post-inflammatory fibrosis is a principal cause of pathology include, but are not limited to, bleomycin-induced pulmonary fibrosis, chronic allograft rejection, idiopathic fibrosis, hepatic cirrhosis (post-viral or alcoholic), radiation-induced pulmonary fibrosis, and schistosomiasis. Other inflammatory conditions include those in which an inflammatory response is triggered by physical and/or chemical insult, including but not limited to burn injury, including thermal, electrical or chemical burns. Thus, it is understood that the methods of the invention can be utilized to treat various inflammatory conditions such as these non-limiting examples and other inflammatory conditions known to those skilled in the art.

Cardiopathies and cardiovascular diseases include, but are not limited to, coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; and arrhythmias. Cardiopathies and cardiovascular diseases to be treated according to a method of the invention further include, but are not limited to, metabolic myocardial diseases and myocardiomyopathies such as congestive, hypertrophic and restrictive cardiomyopathies. A therapeutic agent linked to a homing molecule of the invention will concentrate in atherosclerotic plaques. Thus, the conjugates and methods of the invention are useful for treating these and other disorders associated with atherosclerotic plaques.

As disclosed herein, it has been surprisingly found that, in addition to targeting atherosclerotic plaques, the LyP-1 peptide exhibits anti-inflammatory activity (see Example II). Thus, a peptide comprising a LyP peptide, for example, SEQ ID NOS:1, 2 or 3 or NXXTX, or a peptidomimetic thereof, can be used itself as an anti-inflammatory agent in methods to treat an inflammatory disease. Additionally, it is understood that methods of utilizing a peptide comprising a LyP peptide, for example, SEQ ID NOS:1, 2 or 3 or NXXTX, for treating an inflammatory condition can optionally further include other agents for treating an inflammatory condition in a combination therapy. Thus, a peptide comprising a LyP peptide, for example, SEQ ID NOS:1, 2 or 3 or NXXTX, can be used alone, in combination with other therapeutic agents for treating an inflammatory condition, or as a conjugate with a therapeutic agent, as desired.

A therapeutic agent useful in a conjugate or method of the invention also can be an anti-thrombotic agent that prevents the formation of a thrombus, which is an aggregation of blood factors, primarily platelets and fibrin with entrapment of cellular elements. Thrombus formation is stimulated by the presence of atheromatous plaques and is the main cause of episodes of acute ischemic heart disease. An anti thrombotic agent useful in the invention can be, without limitation, an inhibitor of the IIb/IIIa integrin (Coller, *Circulation* 92:2373 (1995); a tissue factor inhibitor; a plasminogen activator or an anti thrombin agent.

Since xenograft/transplant rejection is an inflammatory associated condition, a method for treating an inflammatory condition that includes transplant rejection can additionally include the use of an immunosuppressive agent, either alone or as a conjugate. It is understood that an immunosuppressive agent can be useful in chronic prophylactic treatment, which organ transplant recipients typically require for their entire lives, or for treating patients exhibiting one or more symptoms consistent with transplant rejection, or for use as a rescue agent in severe rejection. Immunosuppressive agents useful in the conjugates and methods of the invention encompass, without limitation, steroids including corticosteroids and prednisolone; calcineurin inhibitors such as PROGRAF®, NEORAL1®, RAPAMUNE®, cyclosporine A and other cyclosporines; anti-proliferative agents including CELLCEPT®, IMURAN® (azathioprine) and CERTICAN™ (everolimus); and therapeutic monoclonal antibodies such as OKT3, ATGAM, thymoglobulin and anti-thymocyte globulins, dicluzimab and basiliximab. These and other immunosuppressive agents can be useful alone or in combination with another immunosuppressive agent or other therapeutic agent in the conjugates and methods of the invention.

Anti-inflammatory agents, which are molecules that reduce one or more symptoms of inflammation, also are useful in the conjugates and methods of the invention. Such anti-inflammatory agents include, without limitation, steroids including corticosteroids and immunoglobulins as well as cyclooxygenase inhibitors and other non-steroidal anti-inflammatory drugs. In one embodiment, the anti-inflammatory agent is AGI-1067, a cholesterol-lowering anti-inflammatory agent (AtheroGenics; Atlanta, Ala.).

Calcium antagonists, also known as calcium channel blockers (CCBs), have beneficial effects in many cardiovascular diseases, acting as potent inhibitors of smooth muscle cell proliferation and migration. Additional properties that make these therapeutic agents useful in treating atherosclerosis and other cardiovascular disease include their ability to inhibit calcium influx into the vascular wall; reduce extracellular matrix synthesis; promote uptake and breakdown of low density lipoproteins; protect lipoproteins from oxidative modification; maintain endothelial cell function; and inhibit platelet activation. Among the calcium antagonists, amlodipine is a therapeutic agent with vascular selectivity (Marche et al., *Int. J. Cardiol.* 62 (Suppl.): S17 S22 (1997); Schachter, *Int. J. Cardiol.* 62 (Suppl.): S85 S90 (1997)). Additional calcium antagonists which can serve as therapeutic agents useful in the invention include, without limitation, nicardipine, nifedipine, propanolol, isosorbide dinitrate, diltiazem, and isradipine (Nagler (Ed.) *Calcium Antagonists* pages 157-260 London: Academic Press (1988); Schachter, *Int. J. Cardiol.* 62 (Suppl.): S9 S15 (1997)).

A therapeutic agent useful in the invention also can be an antiviral or antibiotic agent. Numerous studies have reported an association of atherosclerosis and restenosis with particular bacterial and viral infections, especially cytomegalovirus and *Chlamydia pneumoniae* (Cheng and Rivera, *Annals of Pharmacotherapy* 32:1310 1316 (1998)). For prophylactic use in a heart transplant or other patient at high risk of developing atherosclerosis, the patient can be administered a conjugate containing a molecule that selectively homes to atherosclerotic plaques linked to an antiviral agent such as ganciclovir. Additional antiviral agents that can be included in a conjugate or method of the invention include, without limitation, Ribavirin (Virazole, 1 β D ribofuranosyl 1,2,4 triazole 3-carboximide) and recombinant human leukocyte IFN αA/D (Matsumori et al., *Circulation* 71:834 839 (1985); Matsumori et al., *J. Am. Coll. Cardiol.* 9:1320 1325 (1987)).

The conjugates and methods also can be useful for treating atherosclerosis, which, in conjunction with its consequences, constitutes the most common and important cause of disease and death in the western world. Like other occlusive vascular disease, atherosclerosis is characterized by the abnormal accumulation of lipid, inflammatory cells, vascular smooth muscle cells, and extracellular matrix proteins within the intimal space between the endothelial lining and the medial layer (plaque formation). In particular, damage to the endothelium allows entry of cholesterol rich low density lipoproteins (LDLs) into the intima. Lipid is taken up by macrophages in the intima, with excessive lipid accumulating in the intimal macrophages through a receptor-independent pathway that takes up oxidized LDL. Macrophages release lipid into the intima and secrete cytokines that stimulate proliferation. Intimal cells with features of myofibroblasts secrete collagen, causing the plaque to become fibrotic in some cases. As the lesion develops, there is pressure atrophy of the media, and the elastic lamina is disrupted. Further collagen deposition forms a dense fibrous cap to the plaque (fibrolipid plaque), which contains free lipid as well as lipid in macrophages. The fragile endothelium of the plaques often ulcerates, allowing platelet aggregation and thrombosis. Growth factors such as platelet derived growth factor cause further plaque development by stimulating cell proliferation.

Increased proliferation of intimal smooth muscle cells causes myointimal hyperplasia and luminal narrowing. The abnormal cell proliferation which plays a role in neointima formation can result from specific growth factors such as platelet derived growth factor (PDGF), transforming growth factor β1 (TGF (β1) or angiotensin II (Ross, Annu Rev. Physiol. 57:791 (1995); Schwartz et al., Circ. Res. 77:445 (1995); and Gibbons and Dzau, New Eng. J. Med. 330:1431 (1994)). A therapeutic agent useful in the conjugates and methods of the invention for treating a cardiovascular disease such as intimal hyperplasia following angioplasty can be a growth inhibitory agent that reduces or prevents vascular disease by limiting neointimal smooth muscle cell proliferation. For example, a herpes virus thymidine kinase (tk) gene and systemic ganciclovir can be used to kill proliferating cells and limit neointimal formation. In one study, porcine iliofemoral arteries were infected with an adenoviral vector encoding tk and, after exposure to ganciclovir, the neointimal thickening seen following balloon injury was reduced by 50-87% (Ohno et al., Science 265:781 784 (1994); see, also, Guzman et al., Proc. Natl. Acad. Sci., USA 91:10732 10736 (1994); Chang et al., Mol. Med. 1:172 181 (1995); and Simari et al., Circulation 92:1-501 (1995)). Thus, a therapeutic agent useful in the invention can be a cytostatic agent such as, without limitation, thymidine kinase combined with ganciclovir. Additional exemplary therapeutic agents for limiting neointimal formation are described, for example, in U.S. publication 20090191223, which is incorporated herein by reference.

A conjugate or method of the invention also can be useful for treating restenosis, which is the re-narrowing of lumen dimensions that may follow angioplasty, a procedure in which a balloon is inserted into an occluded vessel and then inflated to dilate the area of narrowing. Restenosis occurs in about 30 to 50% of cases over a time course of three to six months and involves cellular hyperplasia within the neointima, the organization of thrombus within the vessel wall, and shrinkage of overall vessel dimensions. Angioplasty denudes the vessel of endothelial cells that would normally generate paracrine inhibitors of vascular smooth muscle migration and proliferation.

The conjugates and methods of the invention also can be used to treat congestive heart failure (CHF), a disorder affecting nearly five million people in the United States alone. Congestive heart failure results when the heart is damaged from atherosclerosis or other conditions such as high blood pressure, myocardial infarction or defective heart valves. The failing heart works inefficiently, causing fluid retention, shortness of breath and fatigue. Thus, for treatment of congestive heart failure, in particular that associated with atherosclerosis, a molecule that selectively homes to atherosclerotic plaques can be linked to a therapeutic agent such as, without limitation, a TNF inhibitor such as the recombinant soluble TNF decoy receptor, EMBREL™ (Immunex Corp.; Seattle, Wash.).

In view of the above, it is understood that a variety of therapeutic agents are useful for treating a cardiovascular disease or stroke or an inflammatory disease according to a method of the invention. One skilled in the art understands that these as well as additional known or other therapeutic agents can be selectively directed to atherosclerotic plaques when incorporated into a conjugate or method of the invention. Furthermore, one skilled in the art of understands that these and other therapeutic agents can be used separately or together in the conjugates and methods of the invention. It further is understood that a conjugate of the invention can contain one or more of such therapeutic agents and that additional components can optionally be included in a conjugate of the invention. As an example, in some cases, it can be desirable to utilize an oligopeptide spacer between the homing molecule and the therapeutic agent. See, for example, Fitzpatrick and Garnett, Anticancer Drug Design 10:1 9 (1995).

The present invention further provides methods of imaging atherosclerotic plaques in a subject by administering to the subject a conjugate containing a detectable moiety linked to a homing molecule that selectively homes to atherosclerotic plaques and/or specifically binds p32/gC1q-R; and detecting the conjugate. In the methods of the invention for imaging atherosclerotic plaques, a homing molecule can home to atherosclerotic plaques in vivo with a selectivity, for example, of at least 5-fold relative to non-recombinant phage or other negative control, and can be, for example, a homing peptide or peptidomimetic. A homing molecule useful for imaging atherosclerotic plaques according to a method of the invention includes, for example, a peptide comprising a LyP peptide, for example, SEQ ID NOS:1, 2 or 3 or NXXTX, or a peptidomimetic thereof. A variety of detectable moieties are useful in the above methods of the invention, including, for example, radionuclides and paramagnetic ions.

The imaging methods of the invention rely on a detectable moiety. As used herein, the term "detectable moiety" refers to any molecule which can be administered in vivo and subsequently detected. Exemplary detectable moieties useful in the conjugates and imaging methods of the invention include paramagnetic ions, radionuclides and fluorescent molecules. Exemplary radionuclides include indium 111, technetium 99, carbon 11, and carbon 13. Fluorescent molecules include, without limitation, fluorescein, allophycocyanin, phycoerythrin, rhodamine, and Texas red. Where a detectable moiety is a gamma ray emitting radionuclide such as indium 113, indium 115 or technetium 99, the conjugate can be visualized using a solid scintillation detector following administration to the subject.

The present invention also provides an isolated peptide or peptidomimetic which has a length of less than 400 residues and includes the amino acid sequence of a LyP peptide, for example, SEQ ID NOS:1, 2 or 3 or NXXTX, or a peptidomimetic thereof. The invention provides, for example, an isolated peptide which has a length of less than 400 residues and includes the amino acid sequence of SEQ ID NO:1. As a non-limiting example, an isolated peptide or peptidomimetic of the invention can be conformationally constrained. An isolated peptide or peptidomimetic of the invention further can have any of a variety of lengths. As non-limiting examples, an isolated peptide or peptidomimetic of the invention can have a length of less than 100 residues, less than 60 residues or less than 20 residues. In one embodiment, an isolated peptide or peptidomimetic of the invention includes the amino acid sequence CXCGNKRTRGCZC (SEQ ID NO:7) or CXGNKRTRGZC (SEQ ID NO:8); CXCNRRTKAGCZC (SEQ ID NO:9) or CXNRRTKAGZC (SEQ ID NO:10); CXCGNRRTKZC (SEQ ID NO:11) or CXGNRRTKZC (SEQ ID NO:12); or CXNXXTXZC (SEQ ID NO:13), or a peptidomimetic thereof, where X=0 to 20 independently selected residues and Z=0 to 20 independently selected residues.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

Thus, the invention provides peptides and peptidomimetics including conformationally constrained, bifunctional and multivalent peptides and peptidomimetics as disclosed below. As used herein, the term "peptide" is used broadly to mean peptides, proteins, fragments of proteins and the like. The term "peptidomimetic," as used herein, means a peptide like molecule that has the activity of the peptide upon which it is structurally based. Such peptidomimetics include chemically modified peptides, peptide like molecules containing non naturally occurring amino acids, and peptoids, and have an activity such as the selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803 861).

A variety of peptidomimetics are known in the art and are encompassed within the invention including, for example, peptide like molecules which contain a constrained amino acid, a non peptide component that mimics peptide secondary structure, or an amide bond isostere. A peptidomimetic that contains a constrained, non naturally occurring amino acid can include, for example, an α methylated amino acid; α,α dialkylglycine or α aminocycloalkane carboxylic acid; an Nα Cα cyclized amino acid; an Nα methylated amino acid; a β or γ amino cycloalkane carboxylic acid; an α,β unsaturated amino acid; a β,β dimethyl or β methyl amino acid; a β substituted 2,3 methano amino acid; an N Cδ or Cα Cδ cyclized amino acid; a substituted proline or another amino acid mimetic. A peptidomimetic which mimics peptide secondary structure can contain, for example, a nonpeptidic β turn mimic; γ turn mimic; mimic of β sheet structure; or mimic of helical structure, each of which is well known in the art. A peptidomimetic also can be a peptide like molecule which contains, for example, an amide bond isostere such as a retro inverso modification; reduced amide bond; methylenethioether or methylene sulfoxide bond; methylene ether bond; ethylene bond; thioamide bond; trans olefin or fluoroolefin bond; 1,5 disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr. Section B*, 35:2331 (1979)). This structural depository is continually updated as new crystal structures are determined and can be screened for compounds having suitable shapes, for example, the same shape as a peptide of the invention, as well as potential geometrical and chemical complementarity to a cognate receptor. Where no crystal structure of a peptide of the invention is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to heart vasculature.

The peptides and peptidomimetics of the invention, including the conformationally constrained, bifunctional and multivalent peptides and peptidomimetics discussed below, can have a variety of lengths. A peptide or peptidomimetic of the invention can have, for example, a relatively short length of less than 10, 11, 12, 13, 14, 15, 16, 17, 18, 19, 20, 21, 22, 23, 24, 25, 30, 35, 40, 45, 50, 60, 70 or 80 residues, and so forth as disclosed herein. A peptide or peptidomimetic of the invention also can be useful in the context of a significantly longer sequence as described further below. As used herein, the term "residue" refers to amino acids or analogs thereof. It is understood that a peptide containing, for example, the amino acid sequence SEQ ID NO: 1 includes the specified amino acids as a contiguous sequence not separated by other amino acids.

An isolated peptide or peptidomimetic of the invention can be, without limitation, cyclic or otherwise conformationally constrained. As used herein in reference to a molecule, the term "conformationally constrained" means a molecule, such as a peptide or peptidomimetic, in which the three dimensional structure is maintained substantially in one spatial arrangement over time. Conformationally constrained molecules can have improved properties such as increased affinity, metabolic stability, membrane permeability or solubility. Methods of conformational constraint are well known in the art and include, without limitation, cyclization.

As used herein in reference to a peptide or peptidomimetic, the term cyclic refers to a structure including an intramolecular bond between two non adjacent amino acids or amino acid analogs. The cyclization can be effected through a covalent or non covalent bond. Intramolecular bonds include, but are not limited to, backbone to backbone, side chain to backbone, and side chain to side chain bonds. Methods of cyclization include, without limitation, formation of a disulfide bond between the side chains of non adjacent amino acids or amino acid analogs; formation of a lactam bond, for example, between a side chain group of one amino acid or analog thereof to the N terminal amine of the amino terminal residue; and formation of lysinonorleucine and dityrosine bonds.

As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

The compositions disclosed herein and the compositions necessary to perform the disclosed methods can be made using any method known to those of skill in the art for that particular reagent or compound unless otherwise specifically noted. For example, the peptides can be chemically synthesized by solid-phase stepwise synthesis. Alternatively, the peptides can be expressed from nucleic acids encoding the peptides, as disclosed herein.

One skilled in the art can readily appreciate that a peptide can be synthesized by standard chemical reactions. Methods of synthesizing peptides are well known to those skilled in the art (Merrifield, *J. Am. Chem. Soc.* 85:2149 (1964); Bodanszky, M., *Principles of Peptide Synthesis* (Springer-Verlag, 1984); Houghten, Proc. Natl. Acad. Sci., USA 82:5131 (1985)). For example, peptides or polypeptides can be chemically synthesized using either Fmoc (9-fluorenylmethyloxycarbonyl) or Boc (tert-butyloxycarbonoyl) chemistry (Applied Biosystems, Inc., Foster City, Calif.). In addition, longer peptides or conjugates, including multivalent conjugates, can be synthesized separately and optionally linked via similar protein chemistry techniques. For example, a peptide can be synthesized and not cleaved from its synthesis resin whereas another fragment of a peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a linked peptide or conjugate (Grant G A (1992) *Synthetic Peptides: A User Guide*. W.H. Freeman and Co., N.Y. (1992); Bodansky M and Trost B., Ed. *Principles of Peptide Synthesis*. Springer-Verlag Inc., NY (1993). Such a method can be used to generate a longer peptide or a peptide comprising multiple copies of a shorter peptide. Alternatively, the peptide can be synthesized in vivo as described herein. Once isolated, these independent peptides can be linked to form a peptide or fragment thereof via similar peptide condensation reactions or other appropriate chemical reactions, including the use of chemical linkers, as desired. Additional methods for linking shorter peptides have been described previously (Abrahmsen L et al., *Biochemistry* 30:4151-4159 (1991); Dawson et al., *Science* 266:776-779 (1994); Baggiolini et al., *FEBS Lett.* 307:97-101 (1992); Clark-Lewis et al., *J. Biol. Chem.* 269:16075-16081 (1994); Clark-Lewis et al., *Biochemistry* 30:3128-3135 (1991); Rajarathnam et al., *Biochemistry* 33:6623-6630 (1994); Schnolzer et al., *Science* 256:221-225 (1992); deLisle Milton et al., *Techniques in Protein Chemistry IV*. Academic Press, New York, pp. 257-267 (1992)).

Alternatively, the standard peptides can be generated by expression in a genetically engineered organism, for example, in *Escherichia coli* or other microorganisms or in cell culture, including but not limited to mammalian cells, insect cells, yeast, and the like. A peptide can be expressed separately as a peptide product, as part of a larger polypeptide from which the peptide can be cut out by proteolysis or chemical cleavage, or in the form of concatenated peptides, which can be maintained as a longer polypeptide with multiple copies or resolved into individual peptide species by proteolysis or chemical cleavage at suitable sites.

Disclosed herein are compositions related to isolated LyP peptides, for example, peptides comprising a LyP peptide such as SEQ ID NOS:1, 2 or 3 or NXXTX. The isolated peptides can comprise, for example, a LyP peptide such as SEQ ID NO:1, 2 or 3 or NXXTX, an amino acid sequence at least about 90% identical to a LyP peptide such as SEQ ID NO:1, 2 or 3 or NXXTX, or the amino acid sequence of a LyP peptide such as SEQ ID NO:1, 2 or 3 or NXXTX having one or more conservative amino acid substitutions, so long as the peptide has anti-inflammatory activity and/or homing activity for atherosclerotic plaques. The peptide can be at least about 90%, 80%, 70%, or 60% identical to the amino acid sequence of a LyP peptide such as SEQ ID NO:1, 2 or 3 or NXXTX, so long as the peptide has anti-inflammatory activity and/or homing activity for atherosclerotic plaques. The peptide can comprise a chimera of the amino acid sequence a LyP peptide such as SEQ ID NO:1, 2 or 3 or NXXTX. Such a chimera can be additive, where sequence of one sequence is added to another sequence, substitutional, where sequence of one sequence is substituted for sequence of another sequence, or a combination. For example, the chimera can contain a LyP peptide such as SEQ ID NO:1, 2 or 3 or NXXTX and independently a variant with one or more conservative amino acid substitutions. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

The amino acid sequence can be linear, circular or cyclic. The amino acid segment can be circularized or cyclized via any suitable linkage, for example, a disulfide bond. The peptide can have any suitable length, such as a length of less than 100 residues, less than 50 residues, less than 20 residues or any other lengths disclosed herein.

The disclosed peptides can have any suitable length. The disclosed peptides can have, for example, a relatively short length of less than 10, 11, 12, 13, 14, 15, 16, 17, 18, 19, 20, 21, 22, 23, 24, 25, 26, 27, 28, 20, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 45, 50, 55, 60, 65, 70, 75, 80, 85, 90, 95, 100 or 200 residues. In further embodiments, a peptide can have a length of 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues, and so forth. As used herein, the term "residue" refers to an amino acid or amino acid analog.

Similarly in other embodiments, the peptide or peptidomimetic portion of a conjugate of the invention has a defined length. The peptide or peptidomimetic portion of the conjugate can have, without limitation, a length of at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 400, 500, 600, 700, 800, 900, 1000 or 2000 residues. In other embodiments, the peptide or peptidomimetic portion of the conjugate has a length of at least 10, 15, 20, 25, 30, 50, 100, 150, 200, 250, or 300 residues. It is understood that the term "peptide or peptidomimetic portion of the conjugate" means the total number of residues in the homing peptide or peptidomimetic and any contiguous protein, peptide or peptidomimetic, such as a therapeutic protein or pro apoptotic peptide.

As this specification discusses various proteins and protein sequences it is understood that the nucleic acids that can encode those protein sequences are also disclosed. This includes all degenerate sequences related to a specific protein sequence, that is, all nucleic acids having a sequence that encodes one particular protein sequence as well as all nucleic acids, including degenerate nucleic acids, encoding the disclosed variants and derivatives of the protein sequences.

Peptidomimetic molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH-(cis and trans), —$COCH_2$—, —CH(OH)$CH_2$—, and —$CHH_2SO$— (these and others can be found, for example, in Spatola, in *Chemistry and Biochemistry of Amino Acids, Peptides, and Proteins*, Weinstein, ed., Marcel Dekker, New York, p. 267 (1983); Spatola et al., Vol. 1, Issue 3,

*Peptide Backbone Modifications* (1983); Morley, *Trends Pharm Sci* pp. 463-468 (1980); Hudson et al., *Int J Pept Prot Res* 14:177-185 (1979) (—CH$_2$NH—, CH$_2$CH$_2$—); Spatola et al., *Life Sci* 38:1243-1249 (1986) (—CHH$_2$—S); Hann *J. Chem. Soc Perkin Trans.* 1307-314 (1982) (—CH—CH—, cis and trans); Almquist et al., *J. Med. Chem.* 23:1392-1398 (1980) (—COCH$_2$—); Jennings-White et al., *Tetrahedron Lett* 23:2533 (1982) (—COCH$_2$—); Szelke et al. European Appln, EP 45665 CA (1982): 97:39405 (1982) (—CH(OH) CH$_2$—); Holladay et al. *Tetrahedron. Lett* 24:4401-4404 (1983) (—C(OH)CH$_2$—); and Hruby *Life Sci* 31:189-199 (1982) (—CH$_2$—S—)). A particularly useful non-peptide linkage is —CH$_2$NH—. It is understood that peptide analogs can have more than one atom between the bond atoms, such as β-alanine, γ-aminobutyric acid, and the like.

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence a LyP peptide such as SEQ ID NO:1, 2 or 3 or NXXTX, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 50 residues, less than 100 residues, less than 150 residues, less than 200 residues, less than 250 residues, less than 300 residues, less than 350 residues, less than 400 residues, less than 450 residues, less than 500 residues, less than 800 residues, less than 1000 residues, and the like.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides, which contain a LyP peptide fused to a second peptide having a separate function. Such bifunctional peptides have at least two functions conferred by different portions of the full-length molecule and can, for example, display anti-angiogenic activity or pro-apoptotic activity in addition to the ability to selectively interact with gC1qR/p32, home to atherosclerotic plaques, and/or exhibit anti-inflammatory activity.

Also disclosed are isolated multivalent peptides that include at least two subsequences each independently containing a peptide (for example, the amino acid sequence a LyP peptide such as SEQ ID NO:1, 2 or 3 or NXXTX, or a conservative variant or peptidomimetic thereof). The multivalent peptide can have, for example, at least 2, at least 3, at least 4, at least 5, at least 6, at least 7, at least 8, at least 9, or at least 10 of such subsequences each independently containing a peptide. In particular embodiments, the multivalent peptide can have 2, 3, 4, 5, 6, 7, 8, 9, 10, 11, 12, 13, 14, 15, 16, 17, 18, 19, 20, or even higher numbers of identical or non-identical subsequences. In a further embodiment, the multivalent peptide can contain identical subsequences, such as repeats of SEQ ID NO:1. In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$ cyclized amino acid; an $N^\alpha$-methylated amino acid; a β- or γ-amino cycloalkane carboxylic acid; an α,β-unsaturated amino acid; a β,β-dimethyl or β-methylamino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of βeta-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., *Acta Crystalloqr.* Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., *J. Chem. Inf. Comput. Sci.* 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with atherosclerotic plaques and/or exhibiting anti-inflammatory activity.

If desired, an isolated peptide such as a LyP peptide can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl) benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

Disclosed herein are compositions useful for directing a moiety to a target. For example, the moiety can be incorporated into a LyP peptide composition. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, micelles, polymeric matrices, non-polymeric matrices or particles such as gold particles, microdevices and nanodevices, and nano-scale semiconductor materials. These and other moieties known in the art can be components of a conjugate.

The moiety in the disclosed LyP peptide compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, for example, where the contrasting agent is ionic or non-ionic. In some embodiments, for instance, the detectable agent comprises a tantalum compound and/or a barium compound, for example, barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, for example, a non-radioactive isotope. For example, Gd can be used as a non-radioactive detectable agent in certain embodiments.

Other examples of detectable agents include molecules which emit or can be caused to emit detectable radiation (for example, fluorescence excitation, radioactive decay, spin resonance excitation, and the like), molecules which affect local electromagnetic fields (for example, magnetic, ferromagnetic, paramagnetic, and/or superparamagnetic species), molecules which absorb or scatter radiation energy (for example, chromophores and/or fluorophores), quantum dots, heavy elements and/or compounds thereof (see, for example, detectable agents described in U.S. Publication No. 2004/0009122). Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include, for example, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY™, Cascade Blue™, Oregon Green™, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH$_3$, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and their use are also described in Haugland, Handbook of Fluorescent Probes and Research Products, Molecular Probes, Eugene Oreg. (1996), and Hermanson, *Bioconjugate Techniques* Chapter 8, Academic Press, San Diego Calif. (1996).

Further examples of radioactive detectable agents include gamma emitters, for example, the gamma emitters In-111, I-125 and I-131, Rhenium-186 and 188, and Br-77 (see, for example, Thakur et al., *Throm Res. Vol.* 9 pg. 345 (1976); Powers et al., *Neurology* Vol. 32 pg. 938 (1982); and U.S. Pat. No. 5,011,686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201. The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N,N',N'',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see for example, WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, for example, gadolinium diethylenetriaminepentaacetic acid, for example, used with magnetic resonance imaging (MRI) (see, for example, De Roos et al., *Int. J. Card. Imaging* Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbium(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (for example, hydroxides, carbonates and/or bicarbonates of sodium, potassium and/or lithium), organic bases, and/or basic amino acids can be used to neutralize acidic groups, for example, to facilitate isolation or purification of the composition.

In a particular embodiment, the detectable agent can be coupled to a LyP peptide in such a way so as not to interfere with the ability of the LyP peptide to interact with gC1qR/p32, specifically home to and/or penetrate atherosclerotic plaques, and/or exhibit anti-inflammatory activity. In some embodiments, the detectable agent can be chemically bound to a LyP peptide. In some embodiments, the detectable agent can be chemically bound to a moiety that is itself chemically bound to a LyP peptide, indirectly linking the imaging and targeting moieties.

In addition to detectable moieties, a moiety can be a therapeutic agent. As used herein, the term "therapeutic agent" means a molecule which has one or more biological activities in a normal or pathologic tissue. A variety of therapeutic agents can be used as a moiety.

As disclosed herein, LyP-1 was found to specifically home to atherosclerotic plaques and to penetrate and accumulate within the plaques. Therefore, a conjugate of a peptide comprising a LyP peptide such as SEQ ID NO:1, 2 or 3 or NXXTX can be linked to a therapeutic moiety such as a thrombolytic drug to target the thrombolytic drug to atherosclerotic plaques. Exemplary thrombolytic drugs include, but are not limited to, tissue plasminogen activator t-PA, alteplase (Activase), reteplase (Retavase), tenecteplase (TNKase), anistreplase (Eminase), streptokinase (Kabikinase, Streptase), staphylokinase, urokinase (Abbokinase), anoteplase, and the like.

A therapeutic agent also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells (see, for example, Martin et al., *Cancer Res.* 60:3218-3224 (2000); Kreitman and Pastan, *Blood* 90:252-259 (1997); Allam et al., *Cancer Res.* 57:2615-2618 (1997); and Osborne and Coronado-Heinsohn, *Cancer J. Sci. Am.* 2:175 (1996)). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β, granulocyte macrophage colony stimulating factor (GM-CSF), granulocyte colony stimulating factor (G-CSF), interferon α (IFN-α); interferon γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof (see, for example, Hagedorn and Bikfalvi, *Crit. Rev. Oncol. Hematol.* 34:89-110 (2000), and Kirsch et al., *J. Neurooncol.* 50:149-163 (2000)).

The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., *Anticancer Res.* 19:4203-4214 (1999)). An anti-angiogenic agent also can inhibit another angiogenic factor such as a member of the fibroblast growth factor family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)) or an angiogenic factor such as angiopoietin-1, a factor that signals through the endothelial cell-specific Tie2 receptor tyrosine kinase (Davis et al., *Cell* 87:1161-1169 (1996); and Suri et al., *Cell* 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., *Cell* 79:315-328 (1994)); O'Reilly et al., *Cell* 88:277-285 (1997); Homandberg et al., *Am. J. Path.* 120:327-332 (1985); Homandberg et-al., *Biochim. Biophys. Acta* 874:61-71 (1986); and O'Reilly et al., *Science* 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

In addition to the anti-inflammatory activity of peptides comprising a LyP peptide such as SEQ ID NO:1, 2 or 3 or NXXTX, such peptides can also be used to target a site of inflammation and to provide additional anti-inflammatory activity at a site of inflammation. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), anti-metabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites, where inflammatory responses are likely to occur. Thus, for example, also disclosed are peptides comprising a LyP peptide such as SEQ ID NO:1, 2 or 3 or NXXTX and further comprising an antimicrobial peptide. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli*, *Pseudomonas aeruginosa* or *Staphylococcus aureus*, or other pathalogical bacteria. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. For example, an antimicrobial peptide can have an amphipathic α-helical structure (see U.S. Pat. No. 5,789,542; Javadpour et al., *J. Med. Chem.* 39:3107-3113 (1996); and Blondelle and Houghten, *Biochem.* 31: 12688-12694 (1992)). An antimicrobial peptide also can be, for example, a β-strand/sheet-forming peptide as described in Mancheno et al., *J. Peptide Res.* 51:142-148 (1998). An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274:—151-155 (1990); and Blondelle and Houghten in Bristol (Ed.), *Annual Reports in Medicinal Chemistry* pages 159-168 Academic Press, San Diego). An antimicrobial peptide also can be an analog of a natural peptide, especially one that retains or enhances amphipathicity.

In one embodiment, disclosed are LyP peptide compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art $_D$(KLAKLAK)$_2$, (SEQ ID NO:14) for example, is an antimicrobial peptide which induces marked mitochondrial swelling at a concentration of 10 μM, significantly less than the concentration required to kill eukaryotic cells. Antimicrobial peptides have been described previously (see, for example, U.S. publication 2008/0014143).

It is understood by those skilled in the art that these and other agents are useful therapeutic agents, which can be used separately or together in the disclosed compositions and methods. Thus, it is understood that a peptide comprising a LyP peptide such as SEQ ID NO:1, 2 or 3 or NXXTX can contain one or more of such therapeutic agents and that additional components can be included as part of the composition, if desired. As a non-limiting example, it can be desirable in some cases to utilize an oligopeptide spacer between a peptide having a LyP peptide such as SEQ ID NO:1, 2 or 3 or NXXTX and the therapeutic agent (Fitzpatrick and Garnett, *Anticancer Drug Des.* 10:1-9 (1995)). Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The peptides of the invention comprising a LyP peptide such as SEQ ID NO:1, 2 or 3 or NXXTX can use any of these or similar agents.

A composition comprising a peptide comprising a LyP peptide such as SEQ ID NO:1, 2 or 3 or NXXTX can be used therapeutically in combination with a pharmaceutically acceptable carrier. Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is generally from about 5 to about 8, for example, from about 7 to about 7.5. Further carriers include sustained release preparations such as semipermeable matrices of solid hydrophobic polymers containing the antibody, which matrices are in the form of shaped articles, for example, films, liposomes or microparticles. It will be apparent to those persons skilled in the art that certain carriers can be selected depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

It is further understood that a variety of routes of administration are useful in the methods of the invention. Such routes encompass systemic and local administration and include, without limitation, oral administration, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants.

It is understood that modifications which do not substantially affect the activity of the various embodiments of this invention are also provided within the definition of the invention provided herein. Accordingly, the following examples are intended to illustrate but not limit the present invention.

Example I

Specific Penetration and Accumulation of a Homing Peptide within Atherosclerotic Plaques of ApoE Deficient Mice This example describes the identification of a homing peptide that homes to atherosclerotic plaques and penetrates and accumulates within the plaques.

The diagnosis and treatment of atherosclerosis is dominated by the detection of arterial occlusions, reversal of these occlusions by physical intervention, and long-term management of lipid metabolism. Much less effort has been directed to developing reagents that can specifically target the cellular and molecular components of atherosclerotic lesions. Yet such reagents could be valuable in specifically delivering imaging agents and therapeutics directly into plaques. Targeted delivery that uses carrier molecules with specific affinity for the target tissue (synaphic targeting) increases the efficacy of the targeted drug, while also reducing side effects (Ruoslahti et al., J. Cell Biol. 188:759-768 (2010))

The propensity of macrophages to take up nanoparticles has been used to image plaque (Nahrendorf et al., Circulation 117:379-387 (2008), and an optical probe activated by proteolytic enzymes that are abundant in the plaque environment has been described (Jaffer et al. Circulation 118:1802-1809 (2008)). However, the tendency of nanoparticles to home in plaques is obscured by non-specific uptake by phagocytes in other tissues, and redundancies in protease expression and specificity tend to limit the selectivity of protease-based approaches.

In vivo phage display (Pasqualini and Ruoslahti, Nature 380:364-366 (1996)) has been used with some success to identify reagents with improved specificity for plaque targeting (Kelly et al., Mol. Imaging Biol. 8:201-207 (2006); Nahrendorf, et al. Circulation 114:1504-1511 (2006); Nahrendorf et al., JACC Cardiovas.c Imaging 2:1213-1222 (2009); Liu et al., Am. J. Pathol. 163:1859-1871 (2003); Nicol et al., FEBS Lett. 583:2100-2107 (2009); Peters et al., Proc. Natl. Acad. Sci. USA 106:9815-9819 (2009); Hong et al., J. Cell. Mol. Med. 12:2003-2014 (2008)). The pentapeptide CREKA (SEQ ID NO:4), which binds to fibrin-fibronectin complexes in clotted plasma (Simberg et al., Proc. Natl. Acad.Sci. USA 104:932-936 (2007)), has been shown to home to plaques (Peters et al., Proc. Natl. Acad. Sci. USA 106:9815-9819 (2009)). Following intravenous injection, CREKA-conjugated (SEQ ID NO:4) micelles bound to the surface of plaques and predominantly concentrated at the shoulders of the plaque, which is a location that is prone to rupture (Peters et al., supra (2009)). An anti-thrombotic agent incorporated into the CREKA (SEQ ID NO:4) micelles also accumulated in plaques to a greater extent than when incorporated into control micelles.

Atheroma-associated macrophages (AAM) in plaques are a prime cell target owing to their role in plaque development and their unique features that are not shared by normal tissue macrophages (Wilson et al., Curr. Vasc. Pharmacol. 7:234-243 (2009)). Consequently, AAM may be a suitable synaphic target.

LyP-1, a cyclic, 9-amino acid tumor-homing peptide (sequence: CGNKRTRGC; SEQ ID NO:1) accumulates in tumor macrophages (Fogal et al., Cancer Res. 68:7210-7218 (2008); Laakkonen et al., Nat. Med. 8:751-755 (2002)). The receptor for LyP-1 is a protein known as p32/gC1q-R (Fogal et al., supra (2008)). This protein is a mitochondrial protein in normal cells, but its expression and subcellular location is altered in many human carcinomas and experimental tumors. In addition to general over-expression of p32 in tumors, p32 is present at the cell surface in tumor cells and stromal cells within tumors. Tumor macrophages and the luminal lining of tumor lymphatics are strongly positive for cell surface p32, and tumor-specific homing of intravenously injected LyP-1 peptide is based on the accumulation of LyP-1 in these cells (Fogal et al., supra (2008)). Atherosclerotic plaques contain p32, particularly in the macrophages and foam cells (Peerschke et al., Mol. Immunol. 41:759-766 (2004))). The present study was to determine whether this plaque p32 would be a suitable receptor for plaque targeting with the LyP-1 peptide.

Materials and Methods.

Peptide Synthesis.

Peptides were synthesized as described (Sugahara et al., *Cancer Cell* 16:510-520 (2009) using an automatic microwave assisted peptide synthesizer (Liberty; CEM, Matthews, N.C.) and purified to greater than 90% purity. The LyP-1 peptide was synthesized with an extra N-terminal cysteine used for the chemoselective ligation.

Preparation of Iron Oxide Nanoworms.

Peptide-coated iron oxide nanoworms (NWs; Park et al., *Proc. Natl. Acad. Sci. USA* 107:981-986 (2010)) were prepared as previously described (Agemy et al., *Blood* 116:2847-2856 (2010)). The nanoworms were about 80 to 110 nm in length and 30 in width. The blood half-life of the LyP-1 NW was 12 hours.

Radiochemistry.

4-[$^{18}$F]Fluorobenzoic acid ([$^{18}$F]FBA) was prepared using modifications from previously published reports (Sutcliffe-Goulden et al., *Eur. J. Nucl. Med. Mol. Imaging* 29:754-759 (2002); Guhlke et al., *Nucl. Med. Biol.* 21:819-825 (1994)). The subsequent N-terminal solid phase radiolabeling of Lyp-1 and ARAL (SEQ ID NO:5) with [$^{18}$F]FBA was achieved following previously published methods (Gagnon et al., *Proc. Natl. Acad. Sci. USA* 106:17904-17909 (2009)). In brief, the cleaved [$^{18}$F]FBA-Lyp-1 and [$^{18}$F]FBA-ARAL (SEQ ID NO:5) mixture were evaporated and the desired radiolabeled peptides were isolated by semi-preparative RP-HPLC (Luna C18, 250 mm×10 mm, Phenomenex, CA). Radiochemical purity of isolated peptides on HPLC were more than 95% and specific activity was >20 GBq/mmol. The collected product was isolated in ethanol/acetic acid and formulated to physiological pH for injection.

Animal Protocols and In Vivo Administration of Reagents.

Atherosclerotic plaques in male and female mice homozygous for the ApoetmlUnc mutation (ApoE-null mice) (The Jackson Laboratory) were induced by maintaining the mice on a high fat diet (Reddick et al., *Arterioscler. Thromb.* 14:141-147 (1994); Maeda et al., *Atherosclerosis* 195:75-82 (2007)) for 6 to 8 months. Healthy aortas were obtained from age-matched C7BL/6 wild-type mice fed on a normal diet. The mice were housed and all procedures performed with the approval and according to standards of the University of California, Santa Barbara and University of California, Davis Institutional Animal Care and Use Committees. To test peptide homing, the mice were injected intravenously via retro-orbital under isoflurane inhalation (isoflurane 2% to 3% vol/vol+2 L/min O2) anesthesia and, when applicable, subsequently perfused with high glucose DMEM through the left ventricle to remove unbound reagent. Tissues were excised and left unfixed or fixed with 4% paraformaldehyde.

Immunohistochemistry and Antibodies.

Fresh frozen OCT-embedded tissue was sectioned at 7 μm, fixed with ice cold acetone, blocked with 4% serum in PBS, and stained with antibodies. The following antibodies were used: anti-mouse p32 (rabbit polyclonal; (Fogal et al., supra (2008)), CD68 (rat monoclonal, eBioscience), CD11b (rat monoclonal, eBioscience), CD31 (rat monoclonal, eBioscience), podoplanin (hamster monoclonal, eBioscience), LYVE-1 (rat monoclonal, eBioscience), anti-FITC-HRP (goal polyclonal, ACRIS). Purified rat IgG2a K isotype control (BD Pharmingen), normal rabbit IgG (R&D) and normal goat IgG (R&D) were used as controls. The following secondary antibodies from Invitrogen were used for detection: goat anti-rat 488/546, goat anti-rabbit 488/546, donkey anti-goat 488/546, goat anti-hamster 546 and goat anti-rat 647.

Primary antibodies were incubated for 1 to 4 hours at room temperature, or at 4° C. to detect cell surface expression. Stained tissue sections were mounted in Vectorshield DAPI-containing mounting media (Vector lab). Immunoperoxidase staining with anti-FITC-HRP was performed using DAB (MP Biomedicals) reaction and the sections were counter-stained with 1% methyl green (Sigma Aldrich).

Microscopy and Imaging Analyses.

Tissue sections were examined under a FluoView™ 500 confocal laser-scanning microscope (Olympus) or BX60 fluorescence microscope with MiroFire camera (Olympus). Whole-tissue uptake of fluorescein-labeled peptides following in vivo circulation was imaged using a 530-nm viewing filter, Illumatool light source (Light Tools Research) and recorded with a Canon XTi DSLR camera.

Flow Cytometry.

Cells from plaques and other tissues were released into suspension by 2-hour incubation at 37° C. in a tissue digestion cocktail containing 450 U/mL collagenase type 1 (Worthington Biochemical), 1 mg/mL soybean trypsin inhibitor (Worthington Biochemical), 4.7 U/mL elastase (Worthington Biochemical), 1 mg/mL DNase 1 (Sigma Aldrich) and 0.5% fetal calf serum (FCS). CD11b PE-Cy5 (rat monoclonal, eBioscience) was used to identify monocytes/macrophages. Positive cells were quantified on GUAVA FACS instrument (Millipore) and data were analyzed using FCS Express Version 3 (De Novo Software).

MR Imaging and Analysis.

Excised tissues from n=3-4 mice per group were fixed in 4% paraformaldehyde (PFA) for 48 hours and embedded in 3% agarose in PBS. The gel-embedded tissues were subjected to T2*-weighted MRI scans with a 7-Tesla MR imager (Bruker Biospin) using a FLASH sequence with flip angle of 30°, TR/TE of 1000/15 ms, 512×512 acquisition, 290 μm slice thickness and 2.9 by 2.9 cm regions of interest extending over the heart, aortic arch and descending aorta. Images were processed in ImageJ software, where regions of interest were drawn within the aortic wall of each image and the signal amplitude recorded and averaged after histogram correction for small variations in image amplitude. After imaging, tissues were sectioned for histological analysis with hematoxylin and eosin staining.

MicroPET Imaging and Biodistribution.

A total of 8 male and female ApoE-null mice on high fat diet (>6 months) and 4 female C57BL/6 wild type mice were used for microPET imaging. Anesthetized animals with 2-3% isoflurane were placed in pairs on the scanner bed and PET acquisitions were obtained as described (Gagnon et al., *Proc. Natl. Acad. Sci. USA* 106:17904-17909 (2009)) using a dedicated small-animal PET scanner (Focus120, Siemens Medical Solutions, USA, Inc.). In vivo PET scans were obtained for one hour immediately after tail vein injection of approximately 150 μCi of the radio-labeled peptides in 150 μL PBS and for 30 minutes at 3 hours after injection. Ex vivo excised aortas attached to the heart were imaged for 30 minutes (3 hours after injection). Acquired one hour histograms were reconstructed to four dynamic images (15 minute intervals) with maximum a posterior (MAP) estimation. The biodistribution of radioactivity in collected organs was measured in a gamma counter (Perkin-Elmer Life Sciences, MA).

Statistical Analysis.

Mean differences between groups were statistically tested using two-tailed Student's unpaired t-test or One-way ANOVA followed by a suitable post hoc test. A P value of less than 0.05 was considered statistically significant.

Isolation of Macrophages from 4T1 Tumors and Spleen.

To produce 4T1 tumors, normal female BALB/c mice were orthotopically injected into the mammary fat pad with $1\times10^6$ 4T1 cells suspended in 100 µL of PBS. All animal experimentation received approval from the Animal Research Committee of University of California, Santa Barbara. Fully grown 4T1 tumors and control spleen were excised from the mice two weeks after inoculation, minced and incubated with tissue digestion cocktail containing 2 mg/mL Collagenase IV (Worthington Biochem Corp) and 1 mg/mL DNAse 1 (Sigma) solution in high glucose DMEM media (Gibco) at 37° C. for 1 hour. Cells were passed through 70 µm nylon mesh cell strainer (BD). CD11b-positive macrophages were isolated using the MACS CD11b-positive microbeads (Miltenyi Biotec).

Isolation of Bone Marrow Cells.

Bone marrow cells were isolated from the tibias and femurs of ApoE mice on high fat diet by flushing high glucose DMEM media (Gibco) using an 18 gauge needle and passed through a 70 µm nylon mesh cell strainer (BD).

Peptide Binding Ex Vivo.

Dead cells were first removed from the cell suspension released from aorta, isolated macrophages from 4T1 tumors and spleen and bone marrow cells using Dead cell removal kit (Miltenyi Biotec). Cells were incubated with 1 nmol of either FAM-LyP-1 or FAM-ARAL (SEQ ID NO:5) for 10 min on ice. After washing, the cell pellets were resuspended in buffer containing 1 µg propidium iodide. Cells positive for FAM and propidium iodide staining were quantified on GUAVA FACS instrument (Millipore) and data were analyzed using FCS Express Version 3 (De Novo Software). The % of viable cells after dead cell removal in each case was >75%.

Results.

Homing of LyP-1 Peptide to Atherosclerotic Plaques In Vivo.

Figure 6:
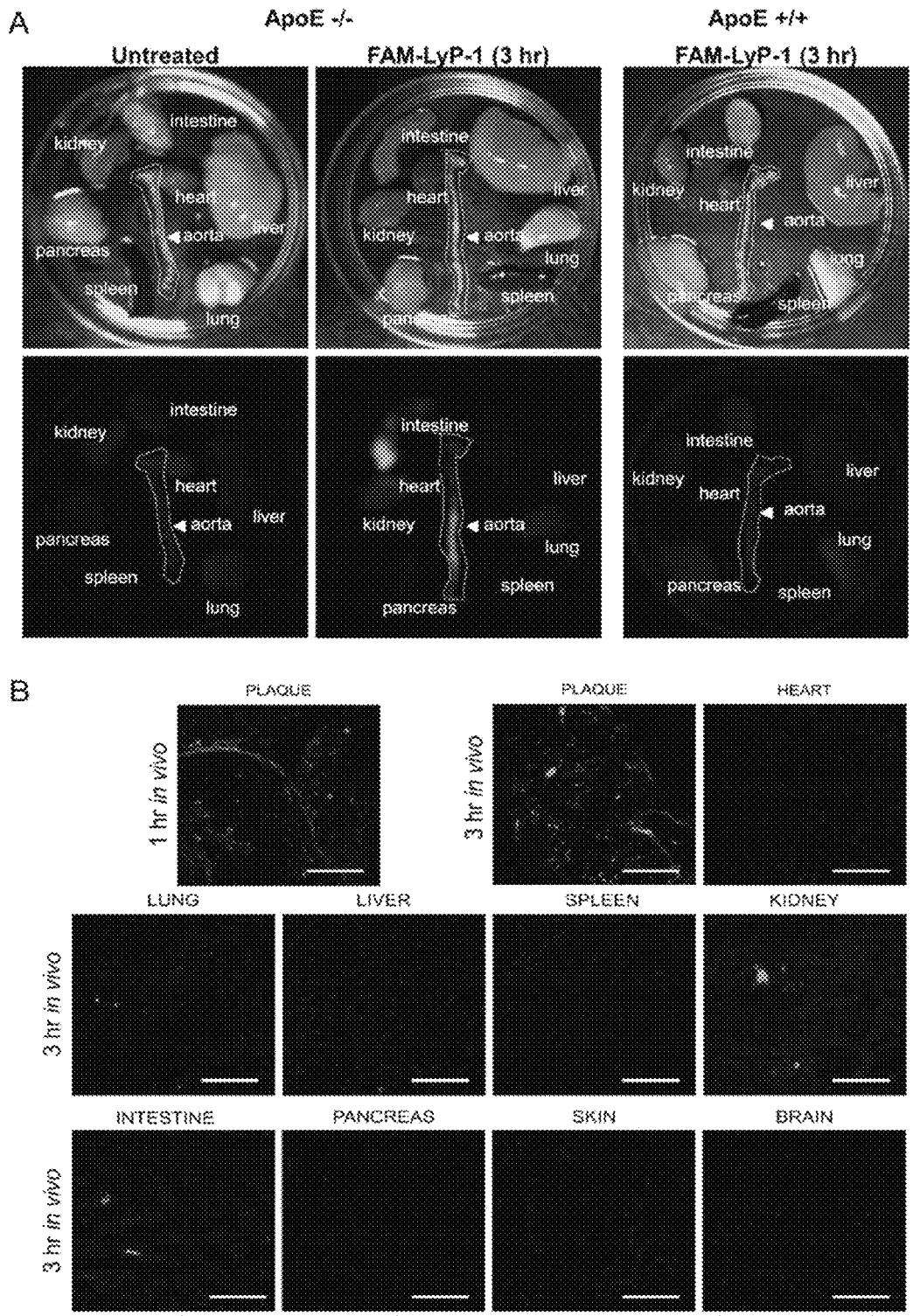
FIGS. 6A and 6B show that LyP-1 specifically homed to aorta containing plaques. Image comparison is of whole-tissue uptake of fluorescein-labeled peptides (FIG. 6A) and tissue cross sections (7 µm) (FIG. 6B) following 3 hour in vivo circulation of LyP-1, highlighting high fluorescence intensity in aorta containing plaques compared to other tissues. Tissue cross section original magnification, ×20. Scale bars, 100 µm.
Figure 7:
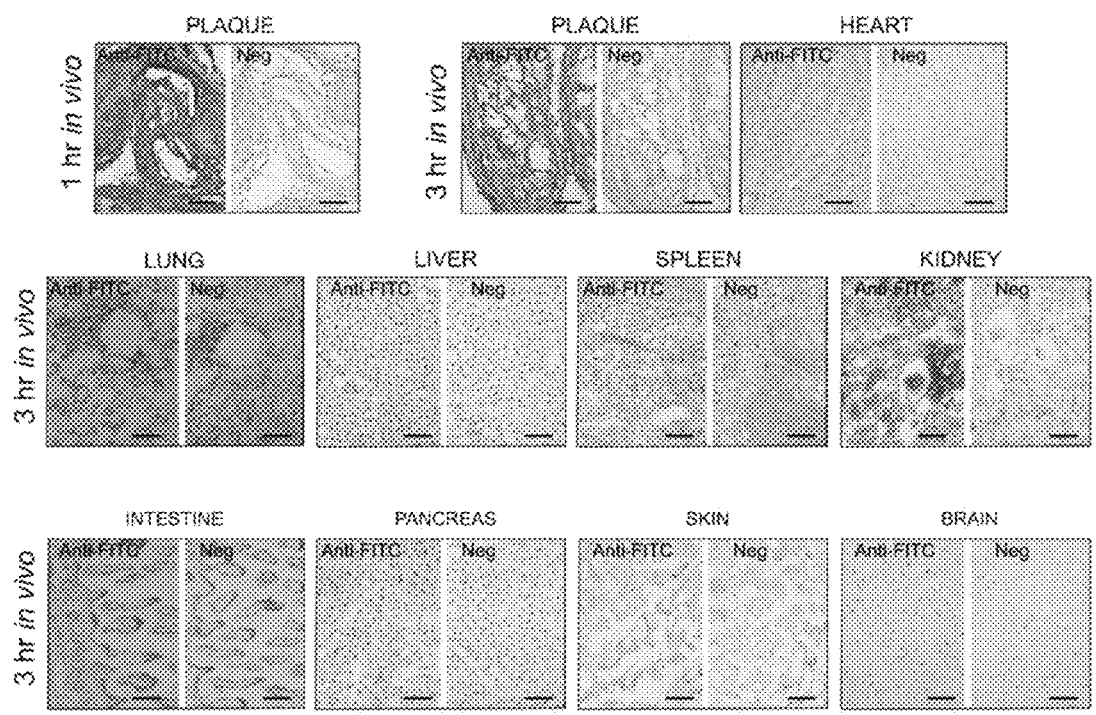
FIG. 7 shows immunoperoxidase staining with an anti-FITC-HRP antibody confirmed LyP-1 accumulation in the plaque compare to other tissues. Original magnification ×20. Scale bars, 100 µm.

To detect peptide homing to plaques, the distribution of intravenously injected peptides that had been labeled with fluorescein (fluorescamine; FAM) were analyzed. Histology analyses of aortas revealed extensive accumulation of FAM-LyP-1 inside the plaque tissue (FIG. 1A). Staining with an anti-fluorescein antibody confirmed the presence of LyP-1 in the plaques. For comparison, mice were also injected with a peptide previously shown to home to plaques, CREKA (SEQ ID NO:4) (Peters et al., *Proc. Natl. Acad. Sci. USA* 106:9815-9819 (2009)). In agreement with the reported results, FAM-CREKA (SEQ ID NO:4) homed to the plaques in a pattern distinct from LyP-1 in that CREKA (SEQ ID NO:4) was essentially confined to the surface of the plaques (FIG. 1A). A control peptide, FAM-ARALPSQRSR (SEQ ID NO:6) (ARAL; SEQ ID NO:5), did not accumulate in the plaques. FACS analysis of cells released from plaques (FIG. 1B) revealed elevated uptake of LyP-1 and CREKA (SEQ ID NO:4) relative to ARAL (SEQ ID NO:5) (% of FAM positive cells; LyP-1, 63.9±5.8; CREKA (SEQ ID NO:4), 18.1±4.6; ARAL (SEQ ID NO:5), 7.5±4.1). LyP-1 accumulation was significantly higher than that of CREKA (SEQ ID NO:4) (P<0.0004). There was no significant accumulation of LyP-1 in healthy aortas and non-aortic tissues of the atherosclerotic mice (FIGS. 1B, 6 and 7).

LyP-1 Targets Atherosclerotic Plaques.

Figure 8:
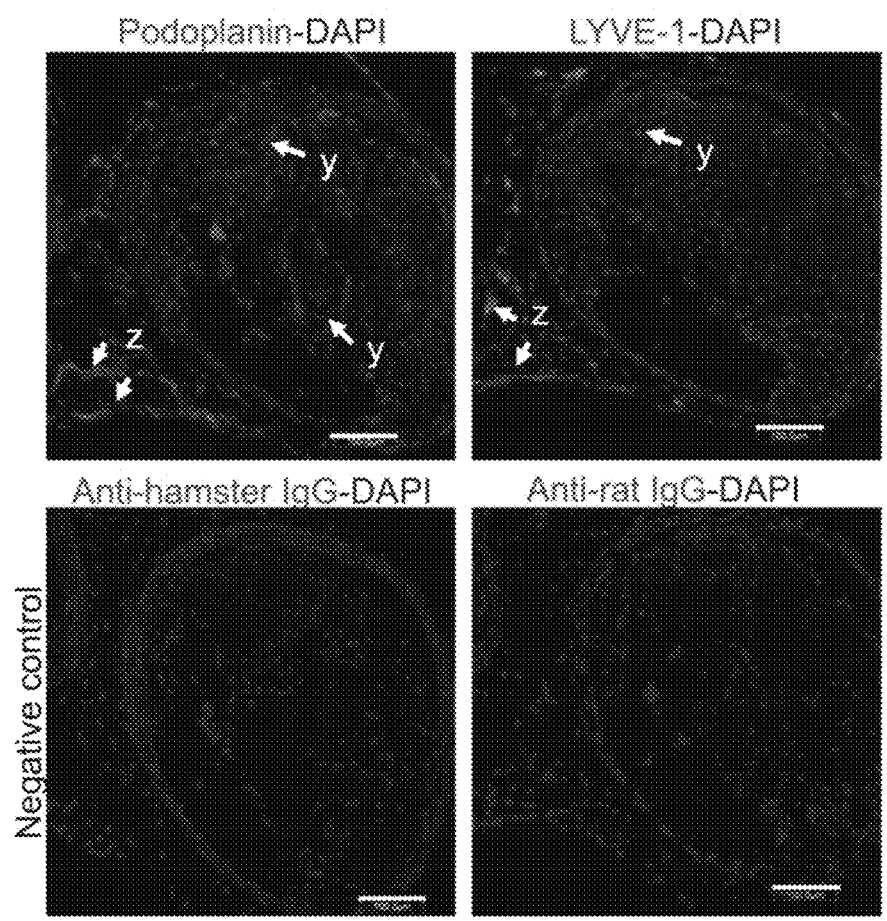
FIG. 8 shows that the adventitia (arrow, z) and interior (arrow, y) of plaques are positive for the lymphatic markers, podoplanin and LYVE-1. IgG controls (hamster and rat) showed negative staining. Original magnification, ×20. Scale bars, 100 µm.

LyP-1 was initially identified as a homing peptide for tumor lymphatics (Fogal et al., *Cancer Res.* 68:7210-7218 (2008); Laakkonen et al., *Nat. Med.* 8:751-755 (2002); Laakkonen et al., *Proc. Natl. Acad. Sci. USA* 101:9381-9386 (2004)). LyP-1 homing in tumors showed strong co-localization with the lymphatic markers, podoplanin and LYVE-1. Hence, experiments were performed to determine whether lymphatic vessels in the plaques were a target for this peptide (14, 15, 17 Fogal et al., supra (2008); Laakkonen et al., supra (2002); Laakkonen et al., supra (2004)). Both plaque adventitia and intima were positive for podoplanin and LYVE-1 (FIG. 8). LyP-1 localized on the luminal surface of plaques (FIG. 2B, panel x) and within areas positive for podoplanin (FIG. 2B, panel y). The podoplanin staining in the interior of plaques showed no co-localization with blood vessel endothelia (CD31) or macrophages (CD11b and CD68)(FIG. 2A). A more widespread accumulation of LyP-1 in the plaque interior was observed in areas positive for macrophages, showing significant co-localization with these cells (FIG. 2C). Analysis of single cells released from plaques 4 hours after intravenous LyP-1 injection (50% of which remained viable after tissue digestion) showed accumulation and internalization of the peptide in CD11b-positive cells (FIG. 2D, FIG. 9). More than 60% of the total CD11b-positive cells were positive for LyP-1 uptake (FIG. 2E; P-value=0.0038 when compared to CREKA (SEQ ID NO:4) and ARAL (SEQ ID NO:5)).

Figure 10:
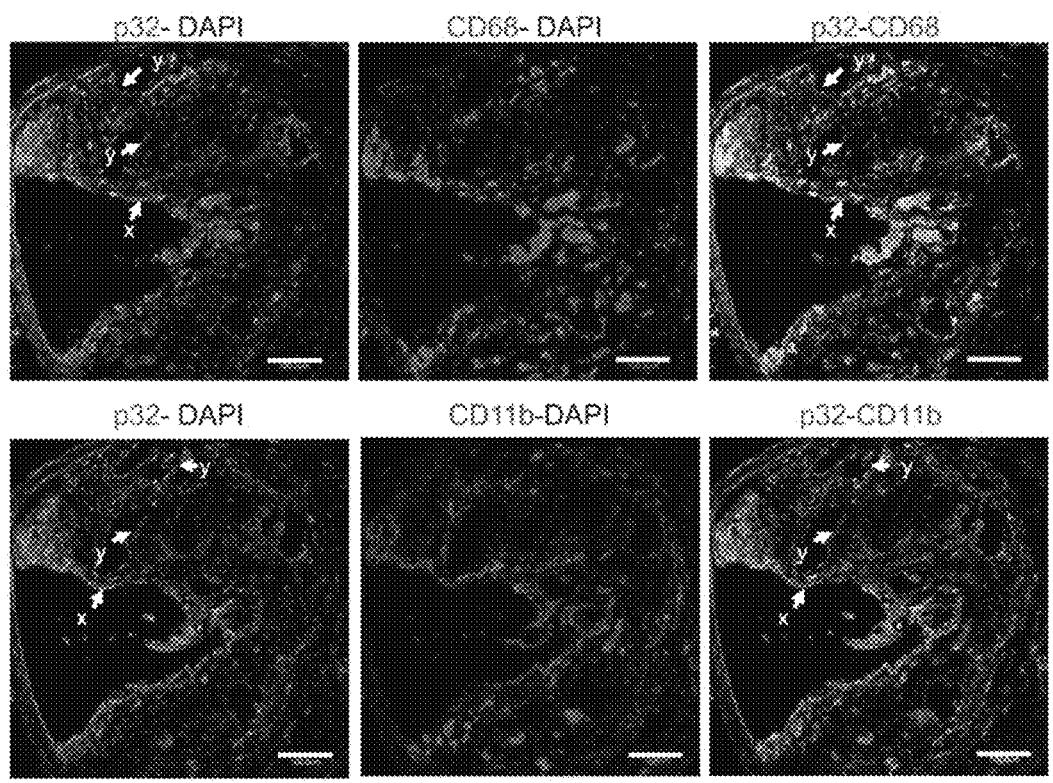
FIG. 10 shows that p32 staining co-localizes predominantly with plaque macrophages. Serial cross-sections of atherosclerotic aortas co-stained with antibodies against p32 (green) and macrophage markers, CD11b and CD68 (red) indicate co-localization of p32 and the macrophage markers. Expression of p32 is also seen on blood vessel endothelia (arrow, x) and lymphatics (arrow, y). These tissues were part of the serial cross-sections shown in FIG. 2A. Original magnification, ×20. Scale bars, 100 µm.

To understand the reasons for the affinity of LyP-1 for atherosclerotic plaques, the expression of receptors associated with LyP-1 binding in plaques was evaluated. Cell surface p32 protein has been shown to be the receptor in tumors that mediates the tumor homing of LyP-1 (Fogal et al., supra (2008)). In accordance with earlier results (Peerschke et al., *Mol. Immunol.* 41:759-766 (2004)), p32 was found to be over-expressed in plaques (FIG. 3A). Immunostaining analysis of non-permeabilized plaque sections and FACS quantification of cells released from plaques indicated p32 expression at the cell surface (FIGS. 3B 3C). In contrast, normal tissues, such as liver and spleen, showed no significant staining prior to permeabilization, but were positive after permeabilization, indicating lack of cell surface localization of p32 (FIG. 3). Histological analysis performed on plaques also showed that p32 was highly expressed on macrophages, endothelia (FIG. 10, panel x) and in areas that were also positive for podoplanin (FIG. 10, panel y). LyP-1 homing co-localized with p32 staining inside plaques (FIG. 3D). Ex vivo analysis of peptide binding to primary cells released from plaques and to CD11b-positive macrophages from 4T1-tumors known to express p32 on the cell surface showed significant binding of LyP-1 to these cells. In contrast, little binding of LyP-1 to normal cells, including monocytes/macrophages isolated from spleen and bone marrow cells, was observed (FIG. 11).

Magnetic Resonance Imaging of Plaque.

Figure 12:
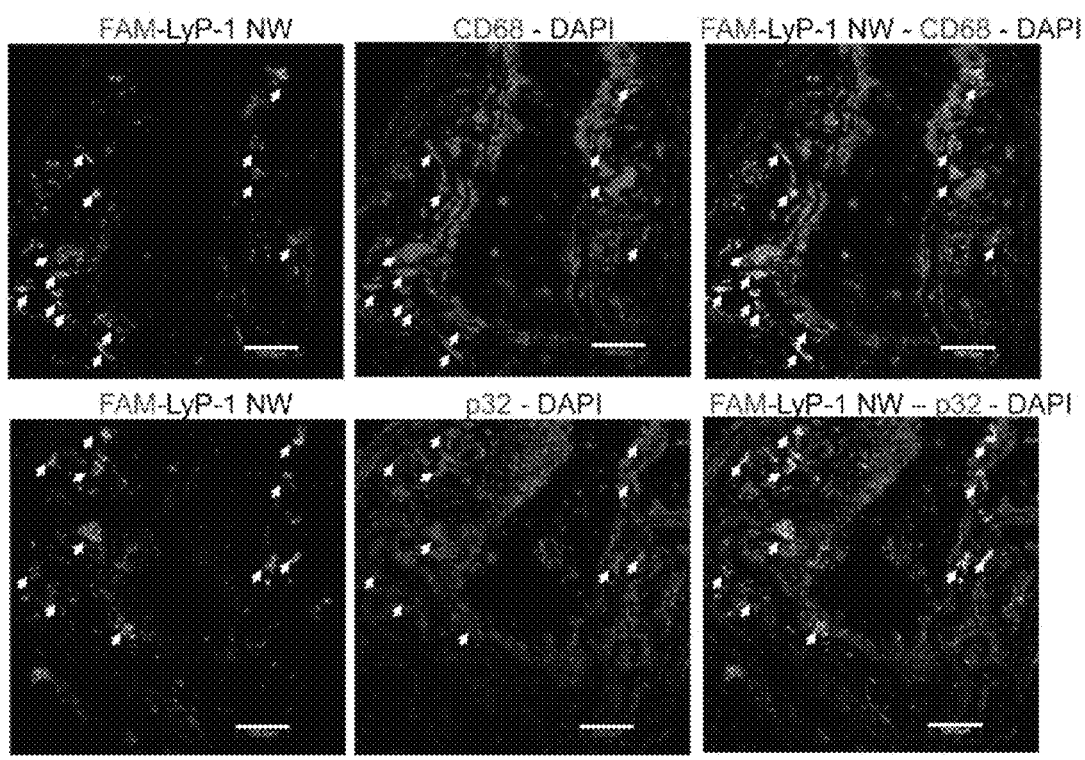
FIG. 12 shows that LyP-1 targeted NWs (green) accumulate in cells predominantly positive for CD68 and p32 (red). Original magnification, ×20. Scale bars, 100 µm.
Figure 13:
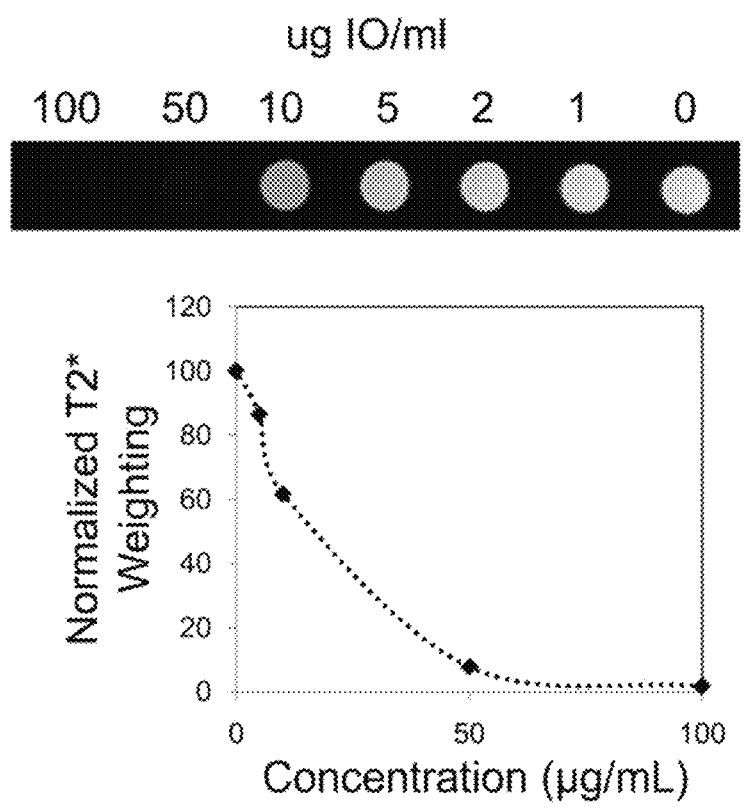
FIG. 13 shows sensitivity of T2* signal for iron oxide NWs with T2*-weighted gradient-echo MRI at 7 T (repetition time, 1000 ms, echo time, 15 ms).

Next, the potential of LyP-1 as a targeting reagent to deliver nanoparticle-based imaging agents to plaques was examined. Intravenously injected LyP-1-coated superparamagnetic iron oxide nanoworms (NWs; (Agemy et al., supra (2010)) accumulated in the interior of plaques (FIG. 4A). The NWs concentrated in cells expressing p32 and CD68 (FIG. 12). In comparison, the accumulation of untargeted NWs was low and limited to the luminal surface of plaques. CREKA-targeted (SEQ ID NO:4) NWs showed greater accumulation on the surface of the plaques, but also only minimally penetrated into the plaques, confirming reported results (Peters et al., *Proc. Natl. Acad. Sci. USA* 106:9815-9819 (2009). Magnetic resonance imaging ex vivo of aortas from mice injected with LyP-1-NWs revealed decreased T2*-weighted signal in areas that contained plaque (FIG. 4B, insets). The axial images of the aorta facilitated a high-resolution comparison with optical imaging and immunohistochemistry, confirming that the NWs were present throughout the plaque volume and that nanoparticle distribution was significantly improved with LyP-1 targeting. Averaging of the T2*-weighted image amplitude throughout the aortic arch and descending aorta indicated that injection of LyP-1-conjugated nanoworms reduced the signal amplitude to a greater extent than CREKA-conjugated nanoworms (40% versus 18%; P<0.01).

MicroPET imaging of 4-[$^{18}$F]Fluorobenzoic Acid Labeled LyP-1.

Figure 14:
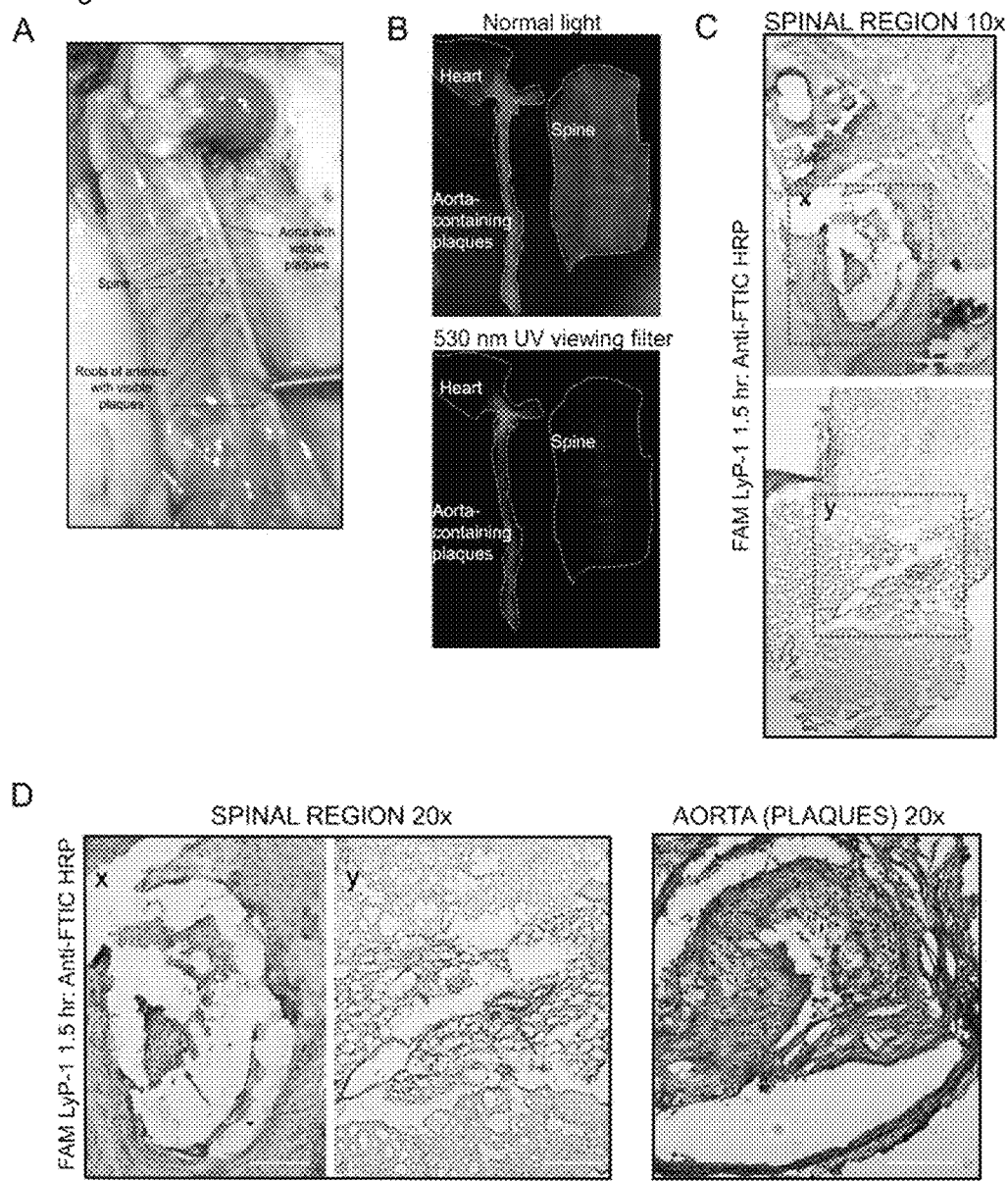
FIGS. 14A-14D show a comparison of LyP-1 accumulation in plaques and in the spine. LyP-1 accumulation in aortic was assessed by measuring the fluorescence from FAM-LyP-1 under a fluorescent microscope and by immunohistochemical detection of FAM (FITC).
Figure 15:
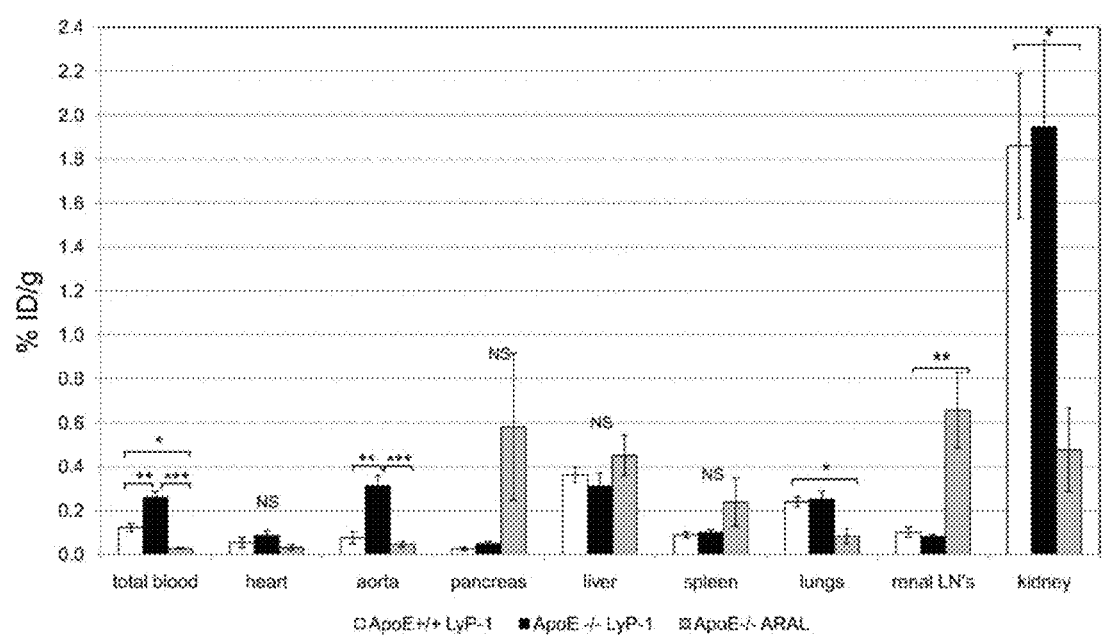
FIG. 15 shows tissue bio-distribution of radiolabeled peptide in each group (n=4 mice per group) measured after 3 hour post-injection. Data are presented as mean±SE percent of injected dose per 1 gram of tissue (% ID/g). P-value, *<0.05, <0.01 and *<0.001.

The potential use of LyP-1 for PET imaging of atherosclerotic plaques was assessed. Dynamic imaging of intravenously injected [$^{18}$F]FBA-LyP-1 over the first hour of circulation highlighted the aorta and the clearance tissues (kidneys and bladder), and radioactivity was also detected in the spine (FIG. 5). The LyP-1 signal detected in the spine was confirmed by histology analysis, but was much smaller than the accumulation in the plaques (FIG. 14). Radioactivity in the reticulo-endothelial system was lower after the injection of [$^{18}$F]FBA-LyP-1 when compared to the control peptide [$^{18}$F]FBA-ARAL (SEQ ID NO:5) (FIG. 5A) and several previously reported [$^{18}$F]FBA-labeled peptides (Gagnon et al., supra (2009)). Excised plaque-containing aortas from mice injected with [$^{18}$F]FBA-LyP-1 showed a stronger PET signal throughout the aortic arch, roots and descending aorta than normal aortas or plaque-containing aortas from mice injected with [$^{18}$F]FBA-ARAL (SEQ ID NO:5) (FIG. 5A). The percent injected dose per gram of tissue (% ID/g) in plaque-containing aortas of [$^{18}$F]FBA-LyP-1 injected mice was 4-fold higher after three hour circulation (Mean±SE; 0.31±0.05) than in aortas from normal mice injected with the same peptide (0.08±0.03; P<0.01) and 6-fold greater than in aortas from atherosclerotic mice injected with the control peptide (0.05±0.01; P<0.001). Accumulation of [$^{18}$F]FBA-LyP-1 was also significantly greater in plaque-containing aortas than in the heart, spleen, pancreas, and renal lymph nodes (<0.1% ID/g; P<0.01; FIG. 5A and FIG. 15). Although not statistically significant, the mean accumulation in plaque-containing aortas was also higher than in the blood (0.26% ID/g), the lungs (0.25% ID/g), and comparable to the liver (0.31% ID/g). Tissue biodistribution data confirmed that the kidneys were the main clearance organ for LyP-1 with mean accumulation of 1.95% ID/g.

These results show plaque homing of a cyclic nanopeptide, LyP-1. The homing is specific; in accordance with earlier studies on the tumor-homing properties of LyP-1 (15, 17 Laakkonen et al., supra (2002); Laakkonen et al., supra (2004)), this peptide showed no accumulation in various normal tissues, including the normal aorta. All plaque-containing regions within the aorta, regardless of the plaque size and volume, were receptive to LyP-1 homing. The analysis indicated that the luminal blood vessel endothelium, lymphatic vessels, and the plaque macrophages were the predominant components positive for LyP-1 accumulation. Importantly, more than 50% of plaque-derived macrophages, a key component of plaques, showed LyP-1 internalization.

A remarkable feature of the LyP-1 homing to atherosclerotic plaques is that circulating LyP-1 penetrates into and accumulates deep within plaque tissue. LyP-1 penetration into the plaque interior is a unique feature not seen with previously-reported plaque homing peptides, which primarily bind to the luminal surface of plaques or to cells close to the luminal surface (Kelly et al., *Mol. Imaging Biol.* 8:201-207 (2006); Nahrendorf, et al. *Circulation* 114:1504-1511 (2006); Liu et al., *Am. J. Pathol.* 163:1859-1871 (2003); Nicol et al., *FEBS Lett.* 583:2100-2107 (2009); Peters et al., *Proc. Natl. Acad. Sci. USA* 106:9815-9819 (2009); Hong et al., *J. Cell. Mol. Med.* 12:2003-2014 (2008)). An example of such peptides is the CREKA (SEQ ID NO:4) peptide in this study, which almost exclusively delivers its payload to the luminal surface of plaques.

Lyp-1 homing shows strong co-localization with the lymphatic markers (podoplanin and LyVE-1) (Fogal et al., supra (2008); Laakkonen et al., supra (2002); Laakkonen et al., supra (2004)). Vessel-like structures were dectected, positive for both of these markers in the plaque intima and even more abundantly in the plaque adventitia. Similar results have been published by others (Nakano et al., *Hum. Pathol.* 36:330-340 (2005)). The affinity of LyP-1 for lymphatics that is presence in the plaques, and the absence of blood vessels in the plaque intima suggest that LyP-1 may enter plaque intima via the lymphatics.

LyP-1 also penetrates into tumor tissue (Fogal et al., supra (2008); Laakkonen et al., supra (2002); Laakkonen et al., supra (2004)). The tumor-penetrating properties of Lyp-1 have been proposed to depend on what has been dubbed the CendR mechanism; after initial binding to tumor vessels, a tumor-homing peptide undergoes proteolytic processing to expose a cryptic CendR motif (R/KXXR/K), the binding of which to neuropilin-1 triggers a transport pathway for extravasation and tissue penetration (Teesalu et al., *Proc. Natl. Acad. Sci. USA* 106:16157-16162 (2009); Sugahara et al., *Science* 328:1031-1035 (2010); Sugahara et al., *Cancer Cell* 16:510-520 (2009)). LyP-1 contains a potential cryptic CendR motif (CGNKRTRGC (SEQ ID NO:1); the bolded residues). Although the involvement of a CendR process in LyP-1 activity remains to be formally proven, it seems likely that this mechanism is responsible for the plaque and tumor penetration.

Previously, p32/gC1qR was identified as the receptor for LyP-1 (Fogal et al., supra (2008)). A previous study has shown that the primary receptor for LyP-1, p32/gC1q-R, is expressed in the endothelial, smooth muscle, and inflammatory cells, such as the foam cells, of the plaque intima and media in human subjects (Peerschke et al., supra (2004)). In this study, it was found that p32 is highly expressed in the atherosclerotic plaques of ApoE-null mice maintained on a high-fat diet. Importantly, it was found that p32 is present both on the cell surface and as an intracellular protein in the plaques. Tumor macrophages, and certain other cells in tumors, also express p32 at the cell surface whereas in normal tissues, p32 is an intracellular (mitochondrial) protein, and not available to bind LyP-1 (shown above, see also Fogal et al., supra (2008); Muta et al., *J. Biol. Chem.* 272:24363-24370 (1997); Dedio et al., *J. Immunol.* 160:3534-3542 (1998)). Consequently, this high cell surface p32 expression, largely on, but not restricted to, plaque macrophages, confers LyP-1 its binding specificity for atherosclerotic plaques.

The role of p32 in disease is poorly understood, but it has been shown to be a critical regulator of the balance between oxidative phosphorylation and glycolysis in tumor cells (Fogal et al., *Mol. Cell. Biol.* 30:1303-1318 (2010)). It has also been suggested that p32 interaction with its ligands may control the differentiation of inflammatory cells such as macrophages and dendritic cells (Hosszu et al., *Innate Immun.* 16:115-127 (2010)). Regardless of what its pathophysiological roles might be, it is clear that cell surface p32 expression and high LyP-1 binding are potentially useful markers for a class of inflammatory cells associated with atherosclerotic plaques and tumors.

The ability of LyP-1 to carry payloads to plaques in delivering PET and MRI contrast agents into plaque was demonstrated. It is noteworthy that the MRI imaging agent was a nanoparticle that is approximately 80 nm long and 30 nm wide, which despite its large size was effectively carried into the interior of the plaques by LyP-1. Iron oxide nanoparticles have previously been used for plaque imaging because they gradually accumulate in the plaque macrophages (Nahrendorf et al. *Circulation* 117:379-387 (2008); Briley-Saebo et al., *J. Am. Coll. Cardiol.* 57:337-347 (2011)). However, within the time frame of this study, no significant accumulation of non-targeted nanoparticles in plaques was found. Also, a previous report (Briley-Saebo et al., supra (2011)) indicated that the intra-plaque macrophage uptake of ~35 nm iron oxide particles is limited by the ability of the particles to traverse through the arterial endothelial wall. The results describe here show that providing the nanoparticles with a LyP-1 coating overcomes this obstacle. In addition, plaques contain cells other than macrophages that are positive for cell surface p32 expression and contribute to the accumulation of Lyp-1 cargo in the plaques. The efficacy of the LyP-1-mediated plaque penetration was underscored by the difference in the localization of LyP-1 and CREKA (SEQ ID NO:4); cargo bound to this previously identified plaque-homing peptide localized to the surface of plaques, but did not penetrate into the interior of the plaques (Peters et al., *Proc. Natl. Acad. Sci. USA* 106: 9815-9819 (2009)).

Plaques were successfully imaged with both MRI and PET in atherosclerotic mice. Ex vivo MRI imaging of the aortic root and the entire descending aorta showed that LyP-1-targeted nanoworms can be imaged in the entire aorta and throughout the plaque interior. In vivo imaging of iron oxide in mouse atherosclerosis has been shown to be feasible and to produce high contrast images (Morris et al., *Arterioscler. Thromb. Vasc. Biol.* 28:265-271 (2008); Guhlke et al., *Nucl. Med. Biol.* 21:819-825 (1994)); however, the typical resolution of in vivo studies is >100 microns (for example, 0.098 $mm^2$ and thus 313 micron in plane resolution (Guhlke et al., supra (1994)), which is not sufficient to differentiate the intra-plaque distribution of LyP-1 and the plaque-surface accumulation of CREKA (SEQ ID NO:4). In addition, PET imaging provided picomolar sensitivity in the imaging of monomeric LyP-1, quantifying the specific accumulation within aortic plaque. The retention of LyP-1 in the spine made it difficult to distinguish between the vascular signal and radioactivity in the spine in the sagittal images, but the two were clearly distinguished in the transverse images. There was a significant difference in the signal density from the plaques and the spine in the immunohistochemistry assay of samples collected later, suggesting appropriate timing of the imaging could eliminate the interference from the spinal signal.

The higher avidity of multivalent LyP-1 constructs could further improve the efficacy of LyP-1-directed PET imaging. While the resolution obtained with PET imaging (~1 mm) is substantially less than that obtained with high field MRI (tens of microns), the exquisite sensitivity in tracking small constructs and the ability to rapidly survey vasculature for small disease foci are advantages with PET molecular imaging. Multi-modal probes will also facilitate future combinations of PET and MRI, in which lesions are detected with PET and mapped at high resolution with MRI (Jarrett et al., *PLoS One* 5:e13254 (2010)).

In conclusion, the LyP-1 peptide shows specific homing to atherosclerotic plaques and penetrates into the interior of the plaques, taking with it payloads ranging in size from small molecules to nanoparticles. Applications in diagnostic imaging, in the assessment of response to therapy and in the delivery of therapeutic compounds into plaques are envisioned.

Example II

Atherosclerotic Plaque Targeting and Anti-Inflammatory Activity of LyP-1 Peptide This example describes targeting of LyP-1 peptide-conjugated micelles to atherosclerotic plaques and anti-inflammatory activity of LyP-1.

Preparation of Micelles.

Peptide-conjugated micelles were prepared as follows. 1,2-Distearoyl-sn-glycero-3-phosphoethanolamine-N-maleimide(polyethylene glycol)2000 (DSPE-PEG2000-Maleimide) and 1,2-distearoyl-sn-glycero-3-phosphoethanolamine-N-methoxy(polyethylene glycol)2000 (DSPE-PEG2000-OMe) in 3:7 molar ratio were dissolved in chloroform in a glass vial. The solvent was evaporated with a thin flow of nitrogen gas. The thin lipid film was hydrated with sterile nitrogen purged water, vortexed and briefly sonicated in a Branson bath sonicator to produce micelles. Peptide (FaM-LyP-1 bearing a free cysteine on its N-terminus) was dissolved in nitrogen purged water and added to the micelles at a peptide: DSPE-PEG2000-Maleimide mole ratio of 1.5:1. The reaction was allowed to proceed at room temperature for 4 hour. Control micelles were reacted with FAM-cysteine. Any non-reacted peptide (cysteine) was removed by extensive dialysis against water using slide-a-lyzer dialysis cassettes (10K MWCO, Pierce). Following dialysis, an appropriate volume of 10× sterile nitrogen purged PBS was added the micellar solution to bring the pH to 7.4. The peptide-conjugated micelles were then sequentially filtered through 0.2 μm PVDF filter (Fisherbrand) and 0.1 μm Anotop 10 filter (Whatman). The sizes of the micelles thus obtained were between 15-18 nm as measured by dynamic laser light scattering on a Malvern Zetasizer Nano (Malvern, UK). The measurements were performed in deionized water with a refractive index of 1.59 and viscosity of 0.89.

The homing of LyP-1 micelles to atherosclerotic plaques was examined. Atherosclerotic mice (ApoE null mice kept on a high-fat diet) were intravenously injected with 200 μL of 1 mM FAM-LyP-1 or control micelles. Three hours later, the aorta was collected and sectioned (7 μm) and fluorescence (green) from the FAM-LyP-1 (FIG. 16, upper panels) and control (FIG. 16, lower panels) micelles was detected in the sections. Autofluorescence signal was detected in the red channel and nuclei were stained with DAPI (blue). As shown in FIG. 16, the LyP-1 micelles were detected in the plaques, whereas only minimal fluorescence was observed in plaques from mice injected with the control micelles.

Figure 17B:
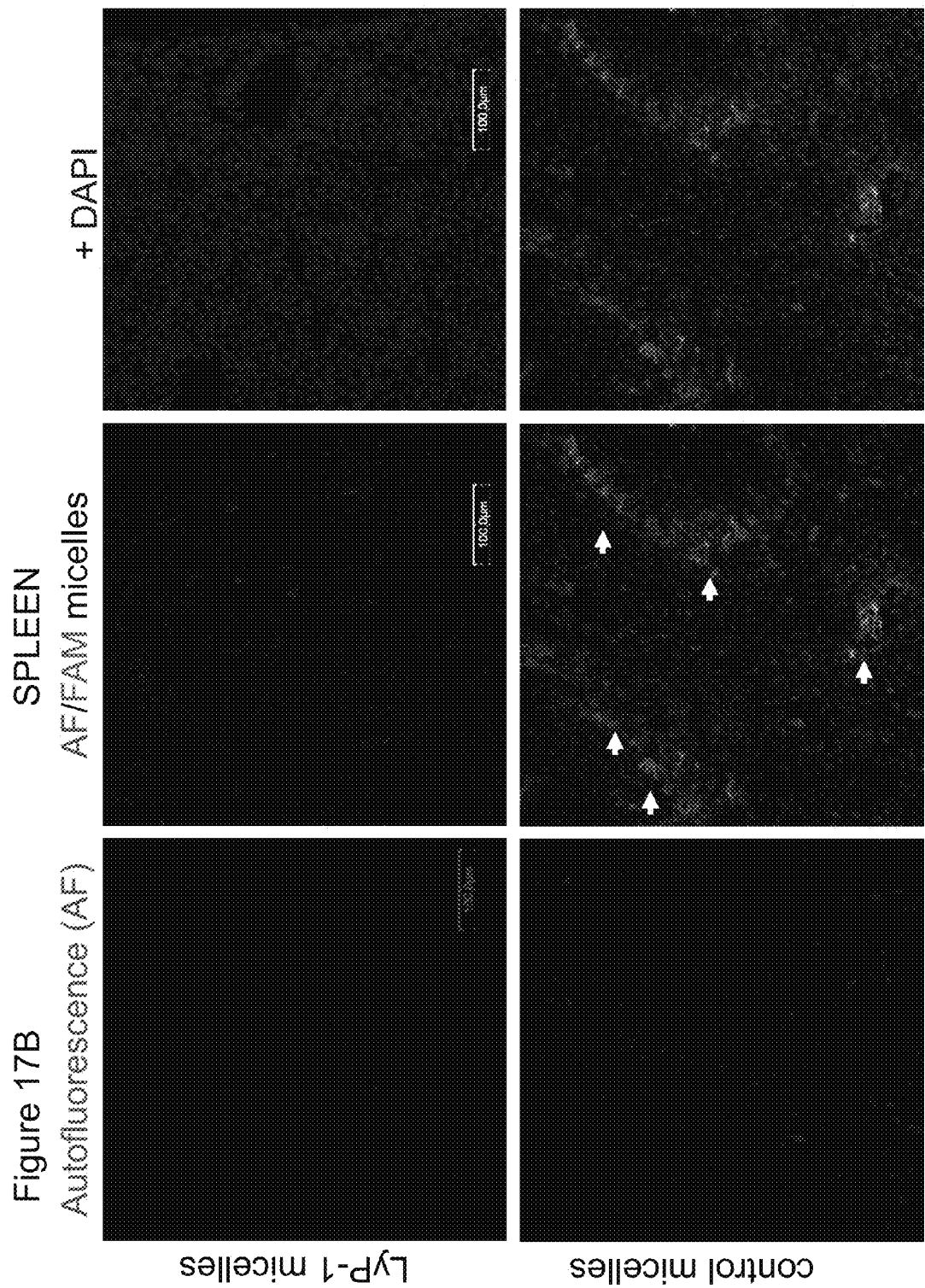

To test for specificity for atherosclerotic plaques, mice were injected with FAM-LyP-1 (FIG. 17, upper panels) and control (FIG. 17, lower panels) micelles as described above, and fluorescence (green) was assessed in liver (FIG. 17A) and spleen (FIG. 17B) sections (7 μm). Autofluorescence signal was detected in the red channel and nuclei were stained with DAPI (blue). The control micelles showed stronger accumulation in the liver (arrows) than the LyP-1 micelles. Thus, low non-specific uptake of LyP-1 micelles was observed in the liver and spleen.

The effect of LyP-1 peptide treatment of mice with tumors was tested. To produce 4T1 breast cancer tumors, normal female BALB/c mice were orthotopically injected into the mammary fat pad with $1 \times 10^6$ 4T1 cells suspended in 100 μL of PBS. The mice were treated with daily tail vein injections of 60 μg of LyP-1 or control peptide (ARALPSQRSR; SEQ ID NO:6) for 12 days. As shown in FIG. 18A, tumor sections were analyzed for CD11b-positive (CD11b+ve) cells (macrophages; green) within the necrotic core, and medial and lateral parts of the tumor. As shown in FIG. 18B, the percentage of cells positive for cell surface expression of the LyP-1 receptor, p32, was determined among CD11b-positive cells (macrophages) in treated 4T1 tumors. Cell suspensions were prepared from 4T1 tumors from mice treated with LyP-1 or the control peptide. The tumors were incubated for 1 hour at 37° C. in a tissue digestion cocktail containing 2 mg/mL Collagenase IV (Worthington Biochem Corp) and 1 mg/mL DNAse 1 (Sigma) in high glucose DMEM media (Gibco). The resulting cell suspension was passed through 70 μm nylon mesh cell strainer (BD), and the live cells were double stained for cell surface p32 (rabbit anti-mouse p32, Fogal et al., supra (2008)) and macrophages (rat anti-mouse CD11b, ebioscience) and analyzed by FACS. The results show that the total number of macrophages and macrophages positive for p32 is reduced in the LyP-1-treated mice.

Figure 19:
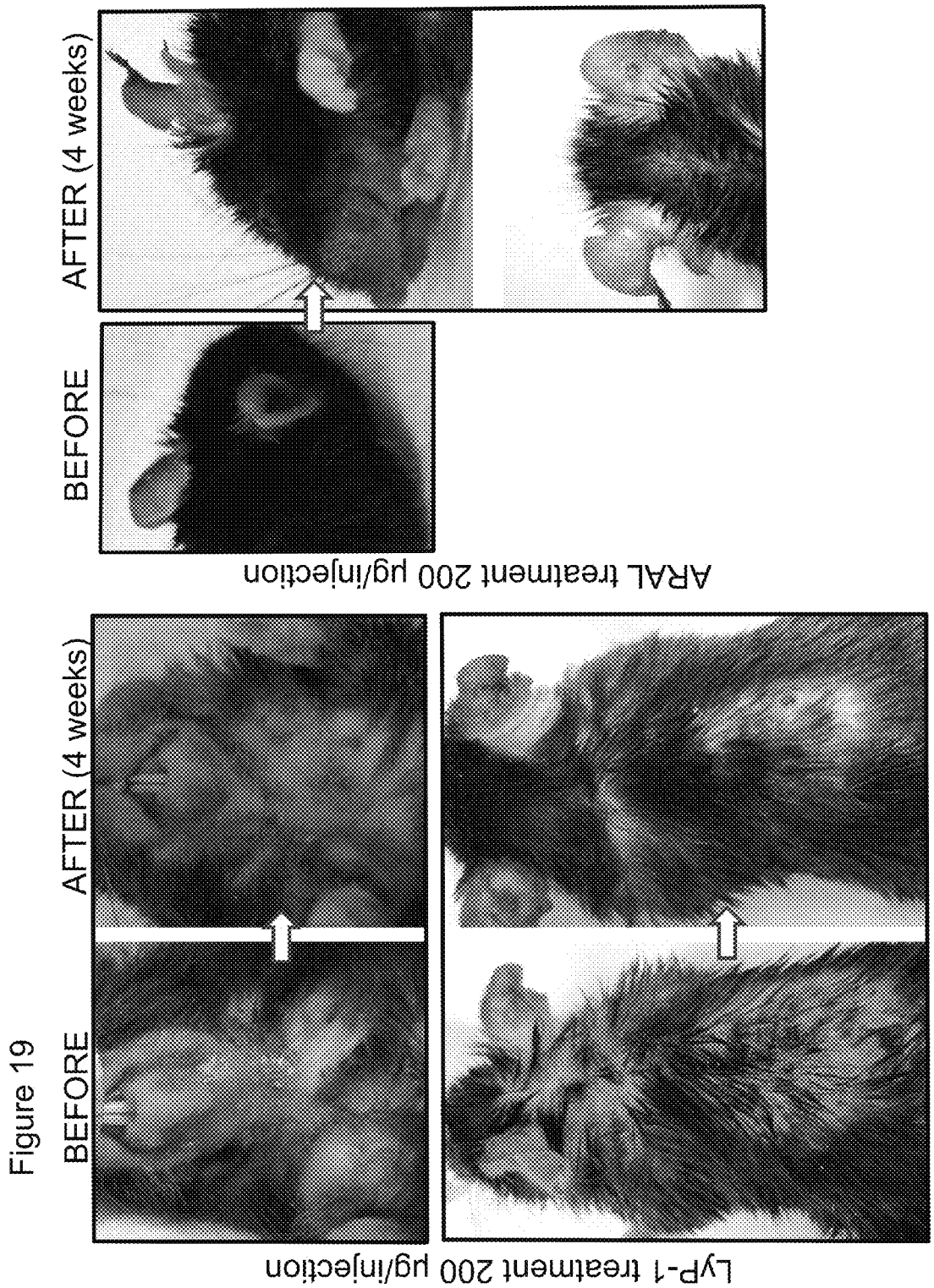
FIG. 19 shows that LyP-1 treatment improves dermatitis. ApoE-null mice that were on a high-fat diet and suffered from severe dermatitis refractory to topical antibiotic treatment were treated with intraperitoneal injections of 200 µg of LyP-1 or control peptide (ARALPSQRSR; SEQ ID NO:6) three times a week for one month (while continuing their diet). The condition of the skin before and after the treatment was recorded in photographs. LyP-1-treated mice (n=5) showed significant improvement of their skin condition. Representative pictures of one mouse in each treatment group are shown.

The effect of LyP-1 treatment on dermatitis was tested. ApoE-null mice that were on a high-fat diet and suffered from severe dermatitis refractory to topical antibiotic treatment were treated with intraperitoneal injections of 200 μg of LyP-1 or control peptide (ARALPSQRSR; SEQ ID NO:6) three times a week for one month (while continuing their diet). The condition of the skin before and after the treatment was recorded in photographs. As shown in FIG. 19, LyP-1-treated mice (n=5) showed significant improvement of their skin condition. Representative pictures of one mouse in each treatment group are shown in FIG. 19. Thus, LyP-1 treatment improves dermatitis.

Figure 20:
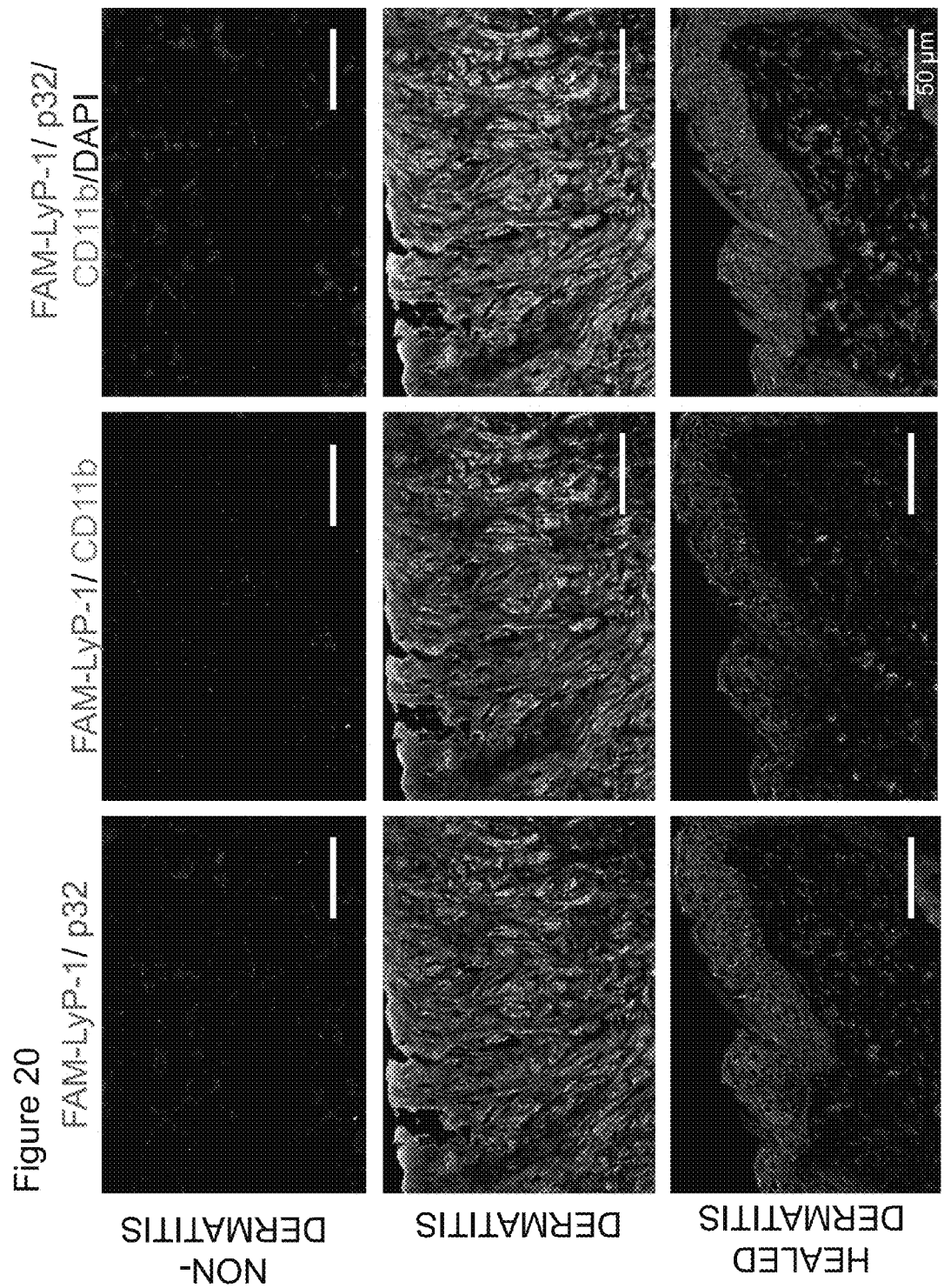
FIG. 20 shows that the effect of LyP-1 on skin dermatitis correlates with reduced p32 expression and macrophage accumulation. Mice treated as in FIG. 19 were intravenously injected with 100 µL of 1 mM fluorescein-labeled LyP-1 and peptide was allowed to circulate for 2 hours. Sections of skin biopsies obtained before and after 4 weeks of LyP-1 treatment were analyzed. Upper row: Normal skin shows no LyP-1 homing (green) and lacks cells positive for p32 (red) and CD11b (magenta) expression. Middle row: Inflamed skin from control-treated mice displays robust LyP-1 homing, particularly in areas rich in CD11b-positive cells that express p32. Lower row: Healed dermatitis skin from LyP-1-treated mice shows reduced thickness, attenuated LyP-1 homing, and smaller numbers of cells positive for CD11b and p32 than the inflamed skin of the control-treated mice. Original magnification ×40. Scale bars, 50 µm. Representative pictures from each treatment group are shown.

The effect of LyP-1 on skin dermatitis correlates with reduced in p32 expression and macrophage accumulation. Mice treated as above in FIG. 19 were intravenously injected with 100 μL of 1 mM fluorescein-labeled LyP-1 and peptide was allowed to circulate for 2 hours. Sections of skin biopsies obtained before and after 4 weeks of LyP-1 treatment were analyzed. As shown in FIG. 20, upper row, normal skin shows no LyP-1 homing (green) and lacks cells positive for p32 (red) and CD11b (magenta) expression. FIG. 20, middle row, shows that inflamed skin from control-treated mice displayed robust LyP-1 homing, particularly in areas rich in CD11b-positive cells that express p32. FIG. 20, lower row, shows that healed dermatitis skin from LyP-1-treated mice shows reduced thickness, attenuated LyP-1 homing, and smaller numbers of cells positive for CD11b and p32 than the inflamed skin of the control-treated mice. Representative pictures from each treatment group are shown in FIG. 20.

Figure 21:
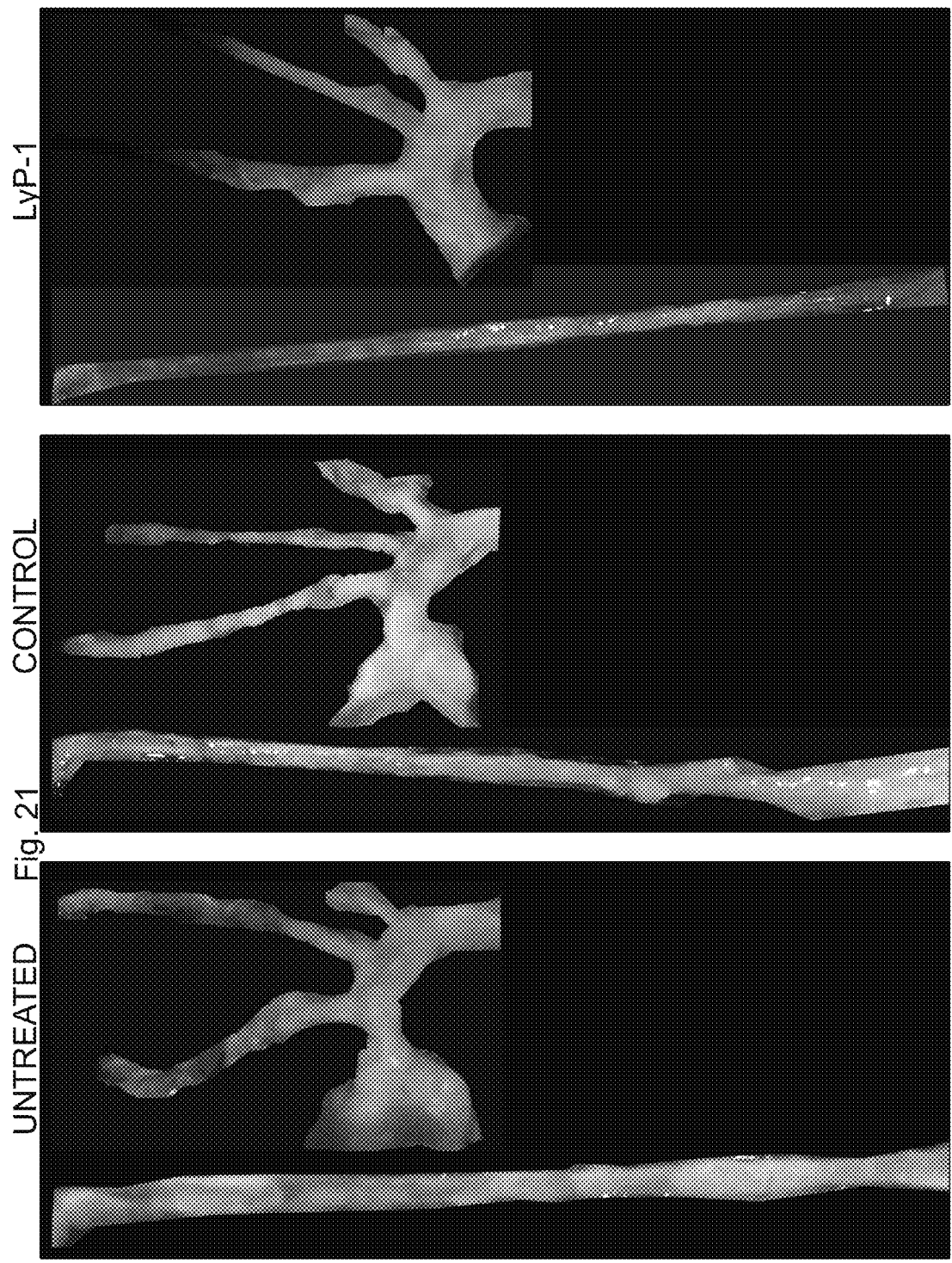
FIG. 21 shows the effect of LyP-1 treatment on plaque formation. ApoE null mice fed a high-fat diet for 5 months were treated with intraperitoneal injections of 200 µg of LyP-1 or control peptide (ARALPSQRSR; SEQ ID NO:6) three times a week for one month (while continuing their diet). Representative images of excised ascending and descending aorta are shown. The LyP-1-treated aortas (n=3) showed reduced plaque formation.

The effect of LyP-1 treatment on plaque formation was tested. ApoE null mice fed a high-fat diet for 5 months were treated with intraperitoneal injections of 200 μg of LyP-1 or control peptide (ARALPSQRSR; SEQ ID NO:6) three times a week for one month (while continuing their diet). FIG. 21 shows representative images of excised ascending and descending aorta. The LyP-1-treated aortas (n=3) showed reduced plaque formation.

Figure 22:
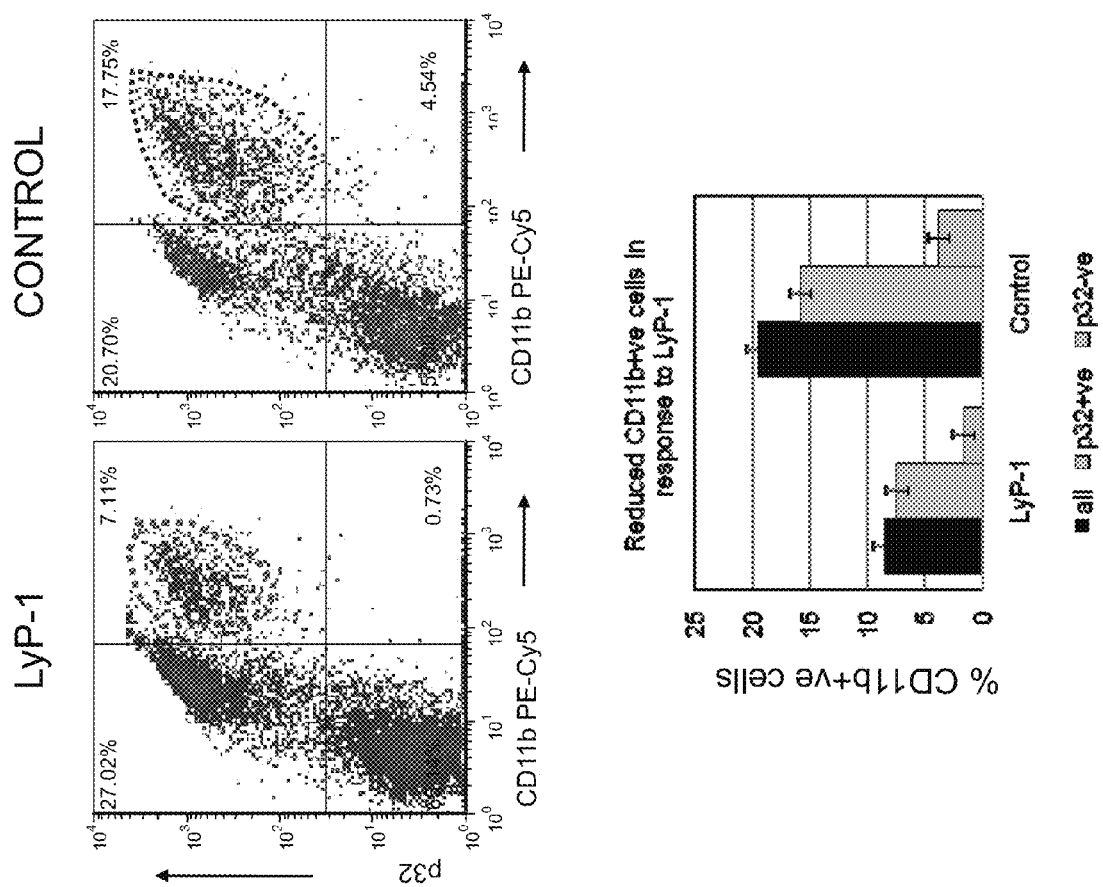
FIG. 22 shows the effect of LyP-1 treatment on plaque macrophages. FACS analysis of cells released from the plaques after 4 weeks of treatment (carried out as in FIG. 21) reveals a lower percentage of total macrophages (p32-positive and negative) in LyP-1-treated aortas than in control-treated aortas. Data are presented as percentage of mean±standard error in each group.

The effect of LyP-1 treatment on plaque macrophages was tested. FACS analysis of cells released from the plaques after 4 weeks of treatment (carried out as described above in FIG. 21) revealed a lower percentage of total macrophages (p32-positive and negative) in LyP-1-treated aortas than in control-treated aortas (see FIG. 22). These results indicate that treatment with LyP-1 resulted in a decrease the number of macrophages released from plaques.

Taken together, these results show that the LyP-1 peptide has an unexpected anti-inflammatory activity. This peptide thus provides a new anti-inflammatory pathway that can be exploited in the treatment of various inflammatory diseases.

Example III

Atherosclerotic Plaque Targeting Activity of LyP-2

This example describes targeting of LyP-2 peptide to atherosclerotic plaques.

The LyP-2 peptide was previously described as homing to lymphatic vessels and tumor cells (Zhang et al., Cancer Res. 66:5696-5706 (2006)).

Figure 23:
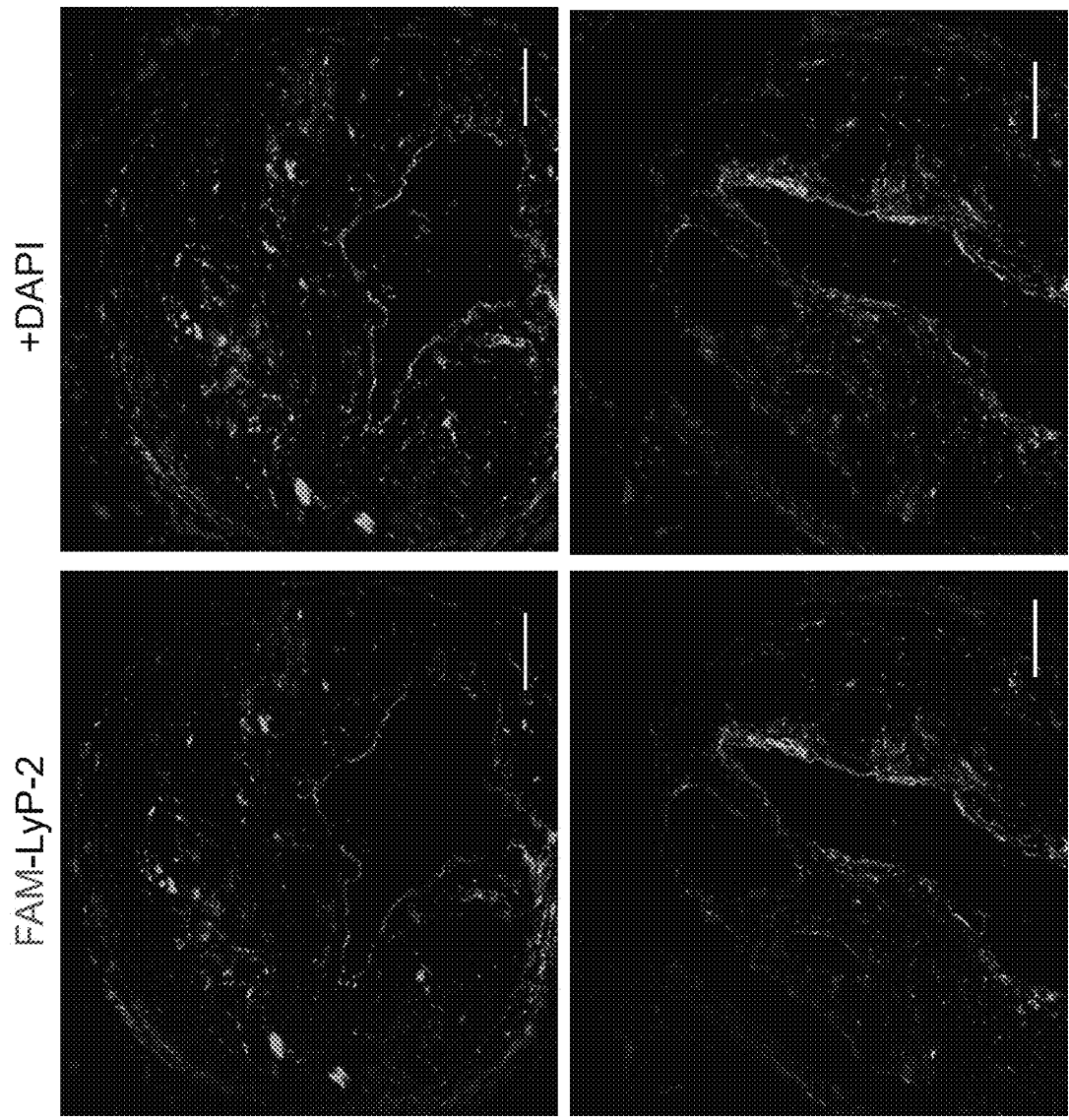
FIG. 23 shows FAM-LyP-2 homing to atherosclerotic plaques. Atherosclerotic mice were injected with 100 µg of FAM-LyP-2, and the probe was allowed to circulate for 1 hour, after which the aorta was collected and the peptide was detected in tissue sections by fluorescence detection.

Atherosclerotic mice were injected with 100 μg of FAM-LyP-2 and the probe was allowed to circulate for 1 hour. Following 1 hour of circulation, the aorta was collected and the peptide was detected in tissue sections by fluorescence detection. Figure X shows accumulation of FAM-LyP-2 (green, upper and lower panel) within plaque tissue (blue, DAPI nuclei staining) Thus, the results shown in FIG. 23 indicate that FAM-LyP-2 homes to atherosclerotic plaques, similar to LyP-1. These results provide additionally exemplary LyP peptides having atherosclerotic plaque homing activity.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of targeting an atherosclerotic plaque in a human subject, the method comprising:
   (a) providing a human subject that has an atherosclerotic plaque; and
   (b) administering a peptide comprising a LyP peptide to the human subject, wherein the LyP peptide comprises the amino acid sequence NXXTX, wherein X can be independently selected from Arg and Lys, and further wherein the peptide has a length of at most 40 amino acid residues, wherein said peptide homes to the atherosclerotic plaque, penetrates the atherosclerotic plaque, and accumulates therein, thereby targeting the atherosclerotic plaque.

2. The method of claim 1, wherein the LyP peptide is in a conjugate linked to a therapeutic agent or a detectable agent.

3. The method of claim 1, wherein the agent is a therapeutic agent.

4. The method of claim 3, wherein the therapeutic agent is a thrombolytic agent.

5. The method of claim 1, wherein the agent is a detectable agent.

6. The method of claim 5, further comprising imaging an atherosclerotic plaque by detecting the detectable agent of the conjugate.

7. The method of claim 1, wherein said LyP peptide comprises an amino acid sequence selected from the group consisting of SEQ ID NO:1, SEQ ID NO:2, and SEQ ID NO:3.

8. A method of targeting an atherosclerotic plaque in a human subject, the method comprising:
   (a) providing a human subject that has an atherosclerotic plaque; and
   (b) administering a peptide comprising a LyP peptide to the human subject, wherein the Lyp peptide comprises an amino acid sequence selected from the group consisting of CXCGNKRTRGCZC (SEQ ID NO:7), CXGNKRTRGZC (SEQ ID NO:8), CXCNRRTKAGCZC (SEQ ID NO:9), CXNRRTKAGZC (SEQ ID NO:10), CXCGNRRTKZC (SEQ ID NO:11), and CXGNRRTKZC (SEQ ID NO:12), wherein X=0 to 20 independently selected residues and Z=0 to 20 independently selected residues, and further wherein the peptide has a length of at most 40 amino acid residues, wherein said peptide homes to the atherosclerotic plaque, penetrates the atherosclerotic plaque, and accumulates therein, thereby targeting the atherosclerotic plaque.

* * * * *

SEQUENCE LISTING

```
<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gly Asn Lys Arg Thr Arg Gly Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Cys Asn Arg Arg Thr Lys Ala Gly Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Asn Arg Arg Thr Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Arg Glu Lys Ala
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Arg Ala Leu
1

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Ala Leu Pro Ser Gln Arg Ser Arg
1               5                   10

<210> SEQ ID NO 7
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (31)..(50)
<223> OTHER INFORMATION: Any amino acid and this region may encompass
```

```
    0-20 residues

<400> SEQUENCE: 7

Cys Xaa Xaa Xaa Xaa Xaa Xaa Xaa Xaa Xaa Xaa Xaa Xaa Xaa
 1               5                  10                  15

Xaa Xaa Xaa Xaa Xaa Cys Gly Asn Lys Arg Thr Arg Gly Cys Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Cys
    50

<210> SEQ ID NO 8
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (29)..(48)
<223> OTHER INFORMATION: Any amino acid and this region may encompass
      0-20 residues

<400> SEQUENCE: 8

Cys Xaa Xaa Xaa Xaa Xaa Xaa Xaa Xaa Xaa Xaa Xaa Xaa Xaa
 1               5                  10                  15

Xaa Xaa Xaa Xaa Xaa Gly Asn Lys Arg Thr Arg Gly Xaa Xaa Xaa
            20                  25                  30

Xaa Xaa Xaa Xaa Xaa Xaa Xaa Xaa Xaa Xaa Xaa Xaa Xaa Xaa
        35                  40                  45

Cys

<210> SEQ ID NO 9
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (31)..(50)
<223> OTHER INFORMATION: Any amino acid and this region may encompass
      0-20 residues

<400> SEQUENCE: 9

Cys Xaa Xaa Xaa Xaa Xaa Xaa Xaa Xaa Xaa Xaa Xaa Xaa Xaa
 1               5                  10                  15

Xaa Xaa Xaa Xaa Xaa Cys Asn Arg Arg Thr Lys Ala Gly Cys Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Cys
```

```
<210> SEQ ID NO 10
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (29)..(48)
<223> OTHER INFORMATION: Any amino acid and this region may encompass
      0-20 residues

<400> SEQUENCE: 10

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Asn Arg Arg Thr Lys Ala Gly Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Cys

<210> SEQ ID NO 11
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (29)..(48)
<223> OTHER INFORMATION: Any amino acid and this region may encompass
      0-20 residues

<400> SEQUENCE: 11

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys Gly Asn Arg Arg Thr Lys Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Cys

<210> SEQ ID NO 12
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
```

```
<220> FEATURE:
<221> NAME/KEY: MOD_RES
<222> LOCATION: (28)..(47)
<223> OTHER INFORMATION: Any amino acid and this region may encompass
      0-20 residues

<400> SEQUENCE: 12

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Asn Arg Arg Thr Lys Xaa Xaa Xaa Xaa
                20                  25                  30

Xaa Xaa Xaa Xaa Xaa Xaa Xaa Xaa Xaa Xaa Xaa Xaa Xaa Xaa Cys
        35                  40                  45

<210> SEQ ID NO 13
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(21)
<223> OTHER INFORMATION: Any amino acid and this region may encompass
      0-20 residues
<220> FEATURE:
<221> NAME/KEY: MOD_RES
<222> LOCATION: (23)..(62)
<223> OTHER INFORMATION: Any amino acid and this region may encompass
      0-40 residues
<220> FEATURE:
<221> NAME/KEY: MOD_RES
<222> LOCATION: (64)..(103)
<223> OTHER INFORMATION: Any amino acid and this region may encompass
      0-40 residues

<400> SEQUENCE: 13

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Asn Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Thr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Cys
            100

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: D-amino acid
```

```
<400> SEQUENCE: 14

Lys Leu Ala Lys Leu Ala Lys Lys Leu Ala Lys Leu Ala Lys
1               5                   10
```